US011653816B2

(12) United States Patent
Ratnakar

(10) Patent No.: US 11,653,816 B2
(45) Date of Patent: May 23, 2023

(54) NEXT GENERATION ENDOSCOPE

(76) Inventor: Nitesh Ratnakar, Elkins, WV (US)

( * ) Notice: Subject to any disclaimer, the term of this patent is extended or adjusted under 35 U.S.C. 154(b) by 0 days.

(21) Appl. No.: 13/043,451

(22) Filed: Mar. 8, 2011

(65) Prior Publication Data
US 2011/0160530 A1    Jun. 30, 2011

Related U.S. Application Data

(63) Continuation-in-part of application No. 10/908,300, filed on May 6, 2005, now Pat. No. 7,621,869, and a continuation-in-part of application No. 10/711,859, filed on Oct. 11, 2004, now Pat. No. 8,585,584.

(51) Int. Cl.
| | | |
|---|---|---|
| A61B 1/012 | (2006.01) | |
| A61B 1/31 | (2006.01) | |
| A61B 1/04 | (2006.01) | |
| A61B 1/018 | (2006.01) | |
| A61B 1/00 | (2006.01) | |
| A61B 1/06 | (2006.01) | |
| G02B 23/24 | (2006.01) | |
| A61B 90/00 | (2016.01) | |

(52) U.S. Cl.
CPC ........ *A61B 1/0005* (2013.01); *A61B 1/00105* (2013.01); *A61B 1/00179* (2013.01); *A61B 1/00181* (2013.01); *A61B 1/018* (2013.01); *A61B 1/0125* (2013.01); *A61B 1/04* (2013.01); *A61B 1/0625* (2022.02); *A61B 1/0676* (2013.01); *A61B 1/31* (2013.01); *G02B 23/2415* (2013.01); *A61B 1/012* (2013.01); *A61B 2090/364* (2016.02)

(58) Field of Classification Search
CPC .............. A61B 1/0005; A61B 1/00177; A61B 1/00179; A61B 1/00181; A61B 1/24; A61B 1/2736
USPC .......... 600/111, 166, 173, 170, 172, 128–130
See application file for complete search history.

(56) References Cited

U.S. PATENT DOCUMENTS

| | | | | |
|---|---|---|---|---|
| 3,703,169 A | * | 11/1972 | Ouchi ................ | A61B 1/00098 385/117 |
| 4,885,634 A | * | 12/1989 | Yabe ............................... | 348/71 |
| 5,547,455 A | * | 8/1996 | McKenna et al. ............ | 600/113 |
| 5,653,677 A | * | 8/1997 | Okada et al. ................. | 600/112 |
| 5,860,912 A | * | 1/1999 | Chiba .......................... | 600/111 |
| 5,928,137 A | * | 7/1999 | Green ................ | A61B 1/00052 600/104 |
| 5,938,585 A | * | 8/1999 | Donofrio ........... | A61B 1/00082 600/116 |
| 5,940,126 A | * | 8/1999 | Kimura ........................ | 348/294 |
| 5,970,980 A | * | 10/1999 | Adair ............................ | 128/849 |

(Continued)

*Primary Examiner* — John P Leubecker
(74) *Attorney, Agent, or Firm* — Kenyon Jenckes

(57) ABSTRACT

An endoscope system includes a shaft portion having a proximal end and a distal end and defining a longitudinal axis. The system also includes a first image receiver coupled to the shaft portion. The first image receiver is directed toward a first direction to receive an image of a first portion of the interior of a lumen. The system also includes a second image receiver coupled to the shaft portion. The second image receiver is directed toward a second direction to receive an image of a second portion of the interior of the lumen. The first direction is generally opposite the second direction. The system further includes a monitor, wherein the image of the first portion and the image of the second portion are displayed simultaneously on the monitor.

5 Claims, 30 Drawing Sheets

(56) References Cited

U.S. PATENT DOCUMENTS

| | | | | |
|---|---|---|---|---|
| 6,066,090 | A * | 5/2000 | Yoon | 600/113 |
| 8,289,381 | B2 * | 10/2012 | Bayer et al. | 348/65 |
| 2005/0070757 | A1 * | 3/2005 | Niwa | A61B 1/00128 |
| | | | | 600/101 |
| 2005/0090709 | A1 * | 4/2005 | Okada | A61B 17/072 |
| | | | | 600/153 |
| 2005/0234296 | A1 * | 10/2005 | Saadat et al. | 600/129 |
| 2006/0106286 | A1 * | 5/2006 | Wendlandt et al. | 600/173 |
| 2006/0149129 | A1 * | 7/2006 | Watts et al. | 600/113 |
| 2007/0032701 | A1 * | 2/2007 | Fowler et al. | 600/173 |
| 2007/0142711 | A1 * | 6/2007 | Bayer et al. | 600/175 |
| 2007/0161855 | A1 * | 7/2007 | Mikkaichi et al. | 600/113 |
| 2007/0185384 | A1 * | 8/2007 | Bayer | A61B 1/005 |
| | | | | 600/129 |
| 2007/0197875 | A1 * | 8/2007 | Osaka | 600/173 |
| 2008/0027279 | A1 * | 1/2008 | Abou El Kheir | 600/111 |
| 2010/0160729 | A1 * | 6/2010 | Smith | A61B 1/00154 |
| | | | | 600/114 |

* cited by examiner

FIG 4B
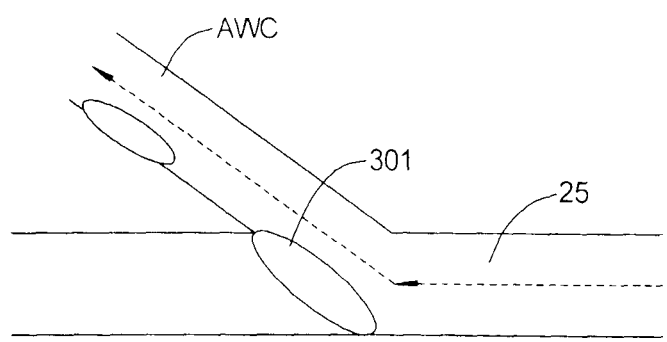
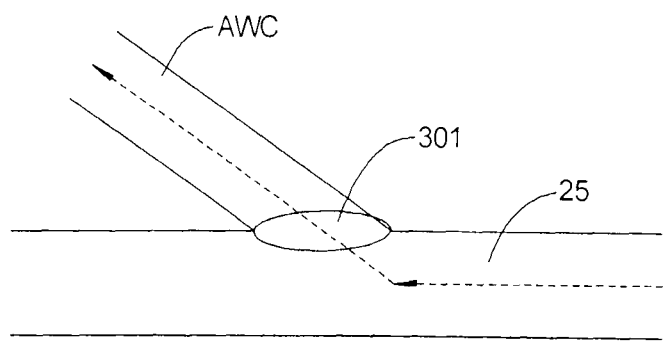
FIG 5A

FIG 22B
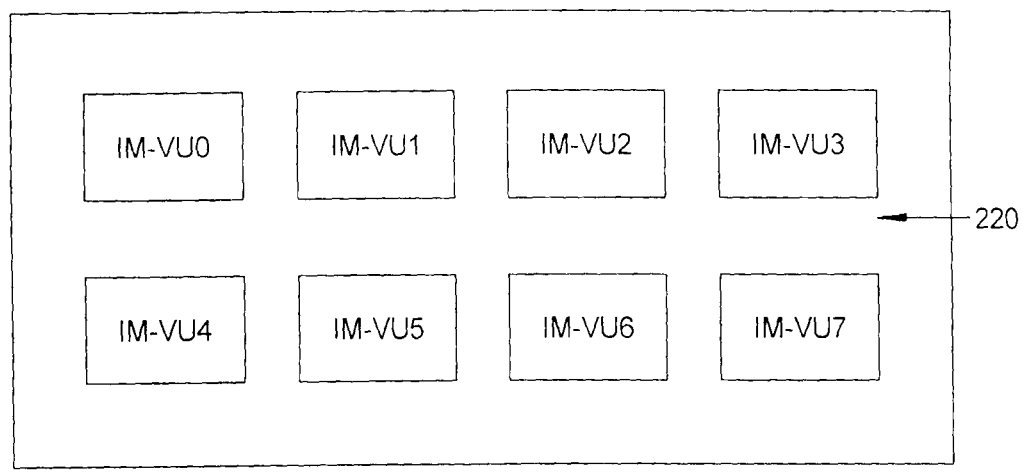
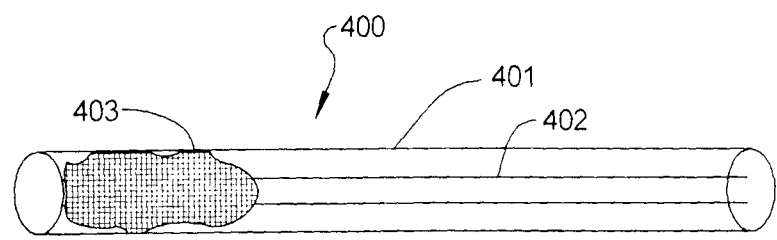
FIG 23A
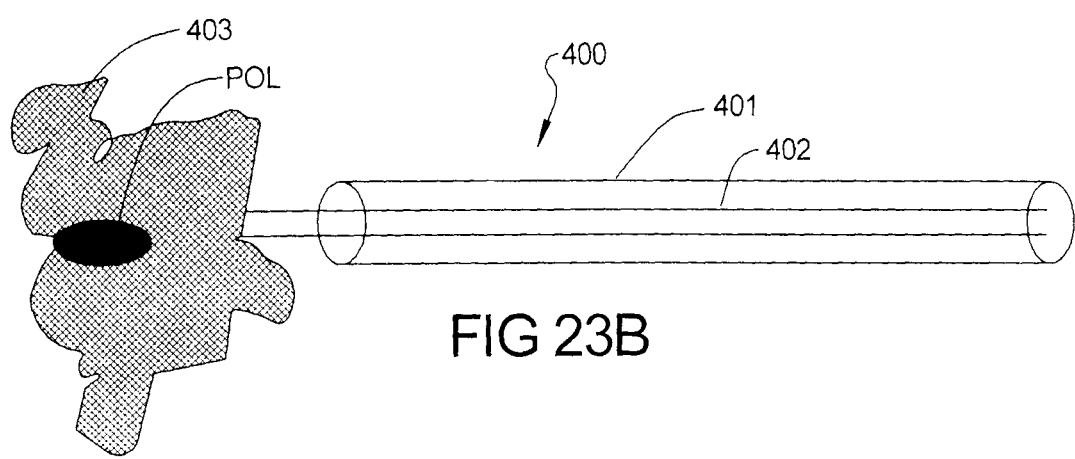
FIG 23B

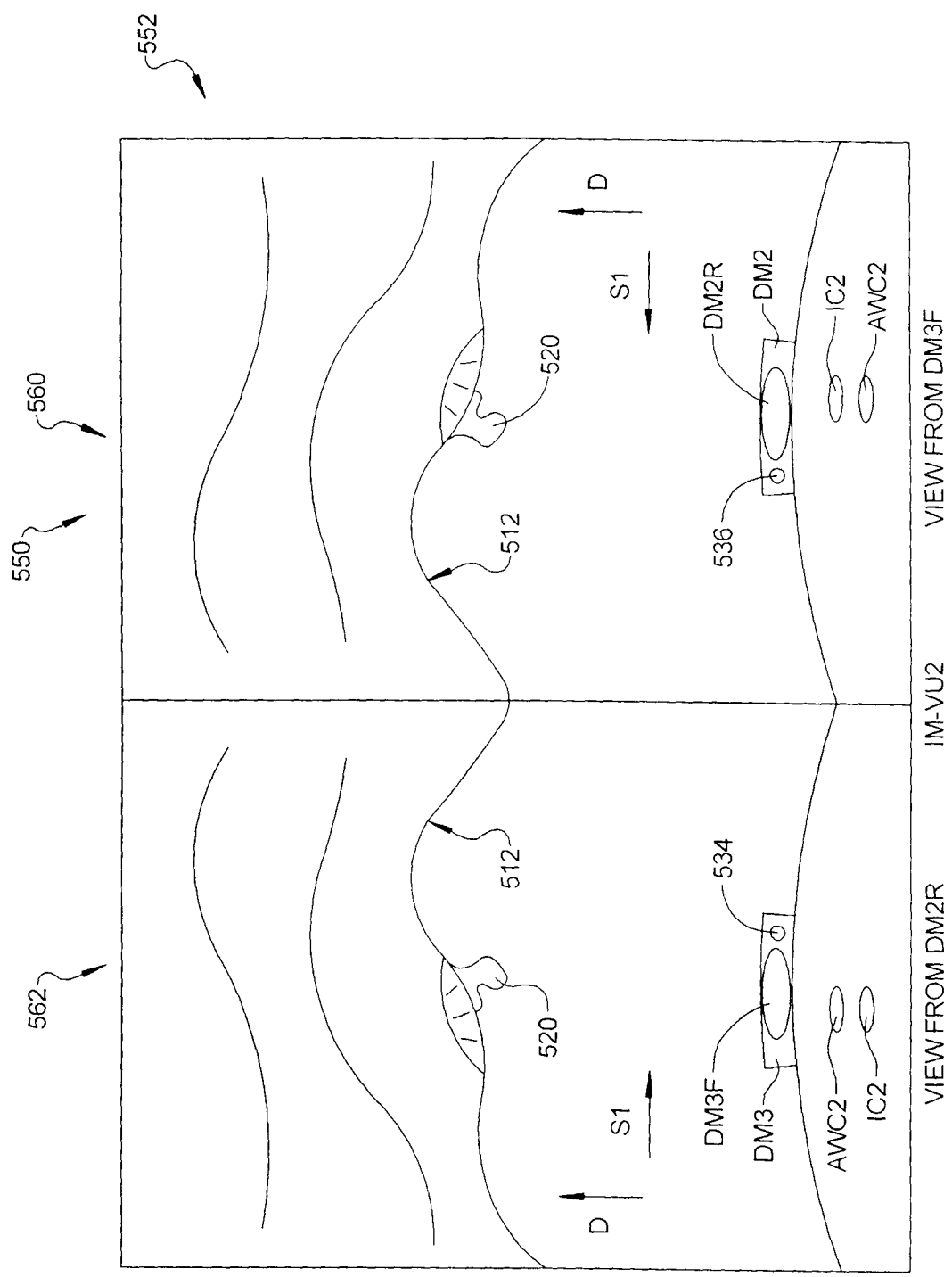

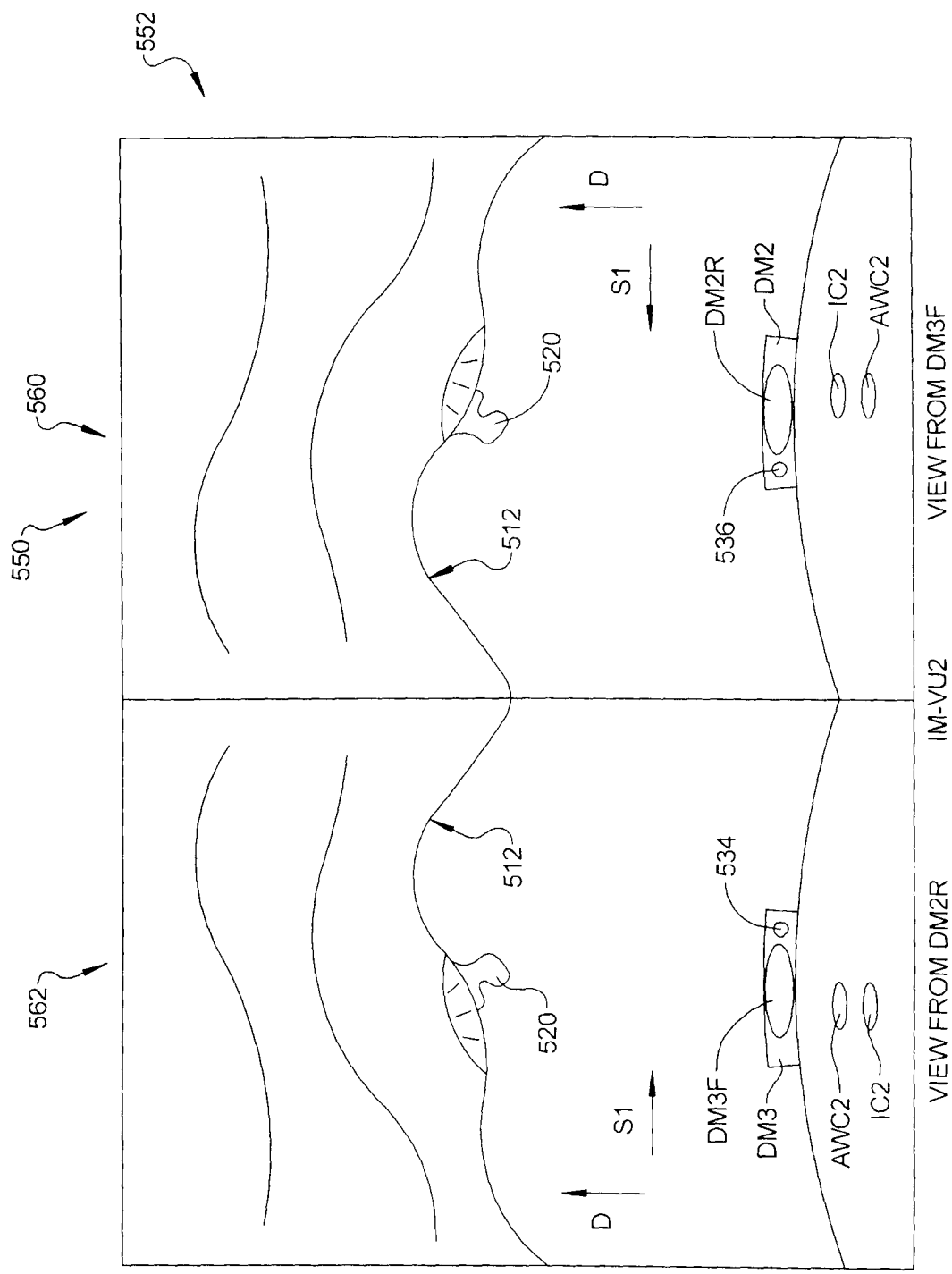

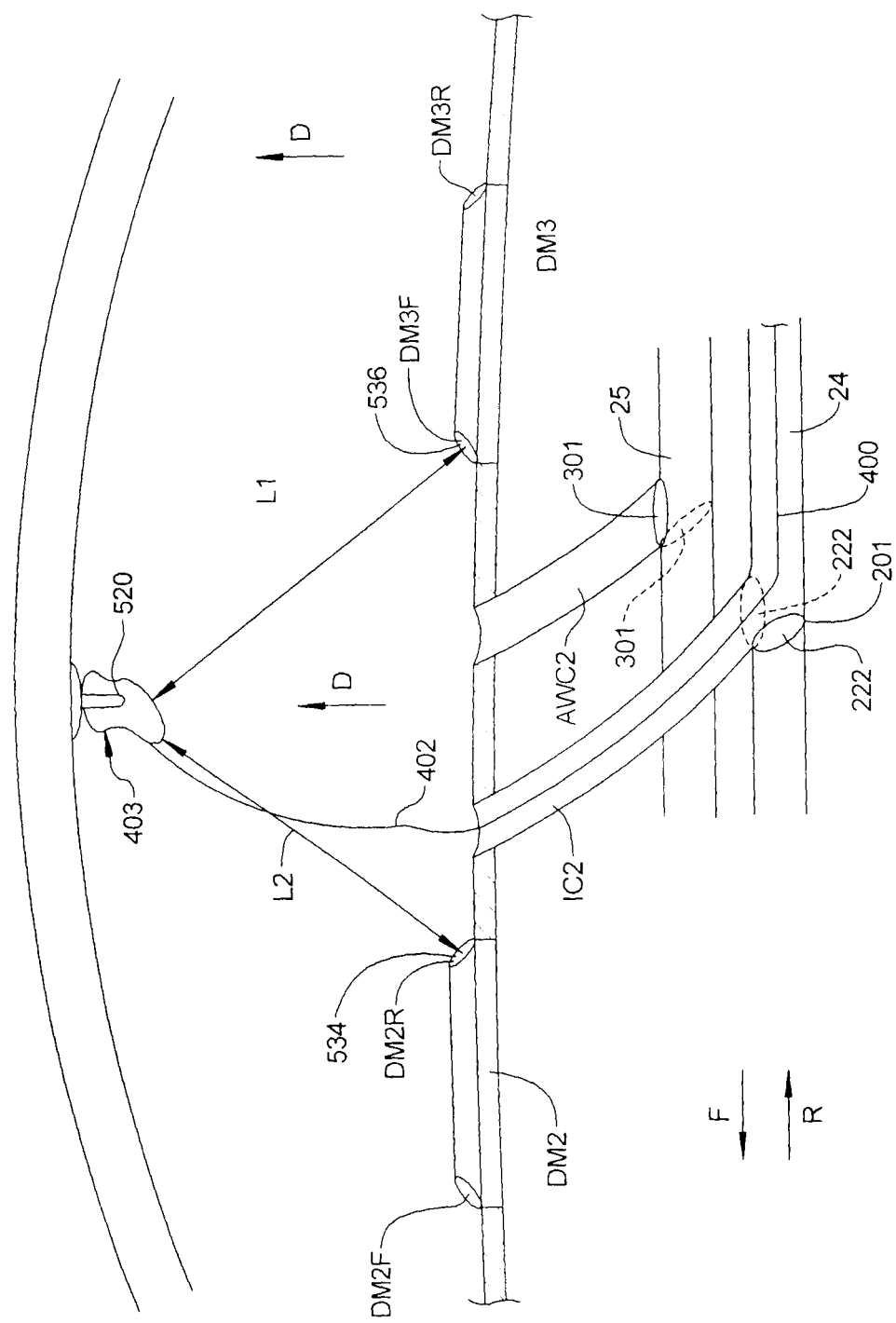

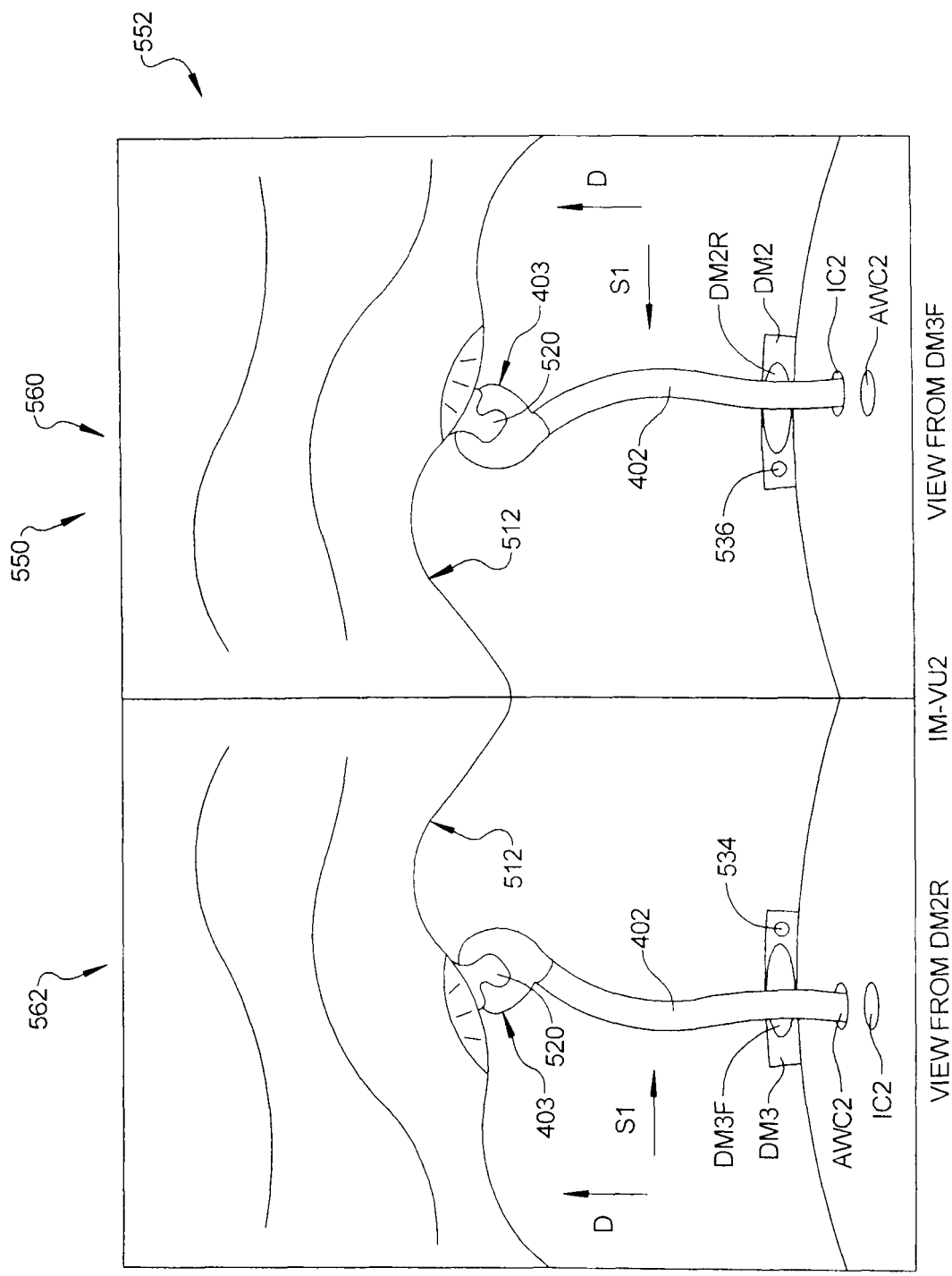

NEXT GENERATION ENDOSCOPE

CROSS REFERENCE TO RELATED APPLICATIONS

This application is a Continuation-in-Part of U.S. application Ser. No. 10/711,859, filed Oct. 11, 2004; and Ser. No. 10/908,300 filed May 5, 2005, the disclosures of which are hereby incorporated by reference in their entirety.

TECHNICAL FIELD

The present invention relates to endoscopes, more specifically to a colonoscope that enables various segments of the colon to he visualized multiple times during a single passage through the colon.

BACKGROUND

Colonoscopes are used to perform a variety of surgical procedures in the colon. FIGS. 1 and 2 illustrate an embodiment of a conventional colonoscope. It has a handle (4) from which extends a flexible shaft (1), which is inserted into a hollow organ to be inspected. The shaft (1) consists of a proximal section (10), insertion tube (6), bending section (12) and a stiff section (13). The shaft terminates in the distal end (14), which typically houses main image lens (20), main illumination bulb (21), air/water nozzle (23) and the main instrument channel outlet (22). The main illumination bulb (21) is connected to a power source by an electric cable (26). The main illumination bulb (21) illuminates the area under the field of view of the main image lens (20). The main image lens (20) captures images of the illuminated area. The image is then transmitted through a fiber optic cable (27) and viewed through an eyepiece (2) on the handle (4) of the colonoscope. Alternatively, the image is transmitted to an image processor (15) by an electrical cable (27). The image is then processed and displayed on a display unit like a computer monitor. The handle (4) of the colonoscope has an extension arm (8) that attaches the colonoscope to a power source and the image processor (15). To enable the colonoscope to maneuver through the turns of a hollow organ, the shaft is flexible and incorporates a multitude of cables that attach the bending portion (12) with actuators (16 & 18). Tension is applied to these cables to move the bending portion (12) of the colonoscope in various directions. This is done by manual adjustment of actuators (16 & 18) on the handle (4) of the colonoscope. Typically, there are two pairs of such cables passing within the shaft, one pair for flexing the bending portion (12) in one plane and the other pair for flexing it in an orthogonal plane. It is also usual to provide two channels extending between the handle and the distal end of the shaft, a main air/water channel (25) and a main instrument channel (24). The main air/water channel (25) is used to insufflate air in a hollow organ to expand it for proper visualization. The main air/water channel (25) is connected proximally to an air/water pump (not shown) and a control switch (3); and distally to the main air/water channel outlet (23). The main image lens (20) and the main illumination bulb (21) are frequently smeared with blood, stool or other body fluids while in a hollow organ which obstructs a clear view. In such a situation, the main air/water channel (25) is used to eject water or blow air at the main image lens (20) and/or main illumination bulb (21) in order to clean them while still inside a hollow organ. The main instrument channel (24) has an inlet (7) proximally and an outlet (22) distally. It is used to pass various surgical instruments to do various surgical procedures. The main instrument channel is also connected to a suction valve (5) proximally and is also used to apply suction to remove fluids, air and other materials from within a hollow organ during examination.

Colonoscope is typically inserted into the patient either thorough a natural body orifice like anus or it is inserted through a surgical incision. It is then steered to a desired location by adjusting the bending portion (2) and manually pushing the colonoscope. After reaching the desired location, which usually is the end of the colon (cecum), the colonoscope is withdrawn. Typically it is during pullout when the inside of a hollow organ like colon is thoroughly examined. Insertion of the colonoscope into a hollow organ is a risky maneuver and is associated with significant complications like trauma, bleeding and perforation. It is generally desirable to complete the examination with a single insertion to minimize complications. The present colonoscopes have significant limitations. Many cancers and pre cancerous lesions (polyps) are frequently missed during colonoscopy (Pickhardt J et al, New England Journal of Medicine 2003; 349: 2191-2200). This has serious consequences including death, many of which can easily be prevented. There are two major reasons why significant lesions are missed during colonoscopy with a conventional colonoscope; 1) majority of the missed lesions lie on the rear side of mucosal folds (Pickhardt J et al; Annals of Internal Medicine 2004; 141: 352-360). With a conventional colonoscope, which is only forward viewing, the front of mucosal folds obstructs visualization of the rear side. Currently, rear side of a mucosal fold can only be examined by pushing the tip of the colonoscope beyond the said mucosal fold and bending it back upon itself in a 'retro flexion' maneuver. However, it is frequently not possible to achieve retro flexion in a narrow hollow organ like colon. Also, retro flexion maneuver compromises the forward view. With a conventional colonoscope, only one view, forward or backward, is passible at a given time Complete examination of colon that includes both forward and rear views currently requires multiple insertions, one to obtain forward view and other to obtain backward view by retro flexion. However, intra colonic retro flexion can't be obtained frequently because colonic lumen is usually very narrow. Moreover, both retro flexion and multiple insertions, independently increase the morbidity, mortality, time and cost of colonoscopy; 2) another factor why lesions are frequently missed, is because conventional colonoscopes enable visualization of a given colonic segment only once. In best scenario, it enables visualization of a given colonic segment twice; once during insertion and once during withdrawl. However, it is to be remembered that traditionally colonic segments are not examined carefully during insertion, as the primary goal at that time is to reach the desired end point It is only during pullout that the colonic segments are examined carefully. Prior studies have shown that multiple-examination of a colonic segment leads to higher detection rate for polyps and cancer during colonoscopy, compared to single examination (Rex D K et al; Gastroenterology. 1997; 112(1): 24-28). Subsequent examination of a colonic segment detects polyps and cancers that were missed during previous examination.

SUMMARY

In view of the significant limitations of the present colonoscope discussed above, there is a need for a colonoscope that would enable thorough and complete examination of the colon. Such a colonoscope will have means to; 1) provide both forward and rear view during a single passage through the colon; and 2) enable examination of a given segment of the colon multiple times, preferably during a single passage through the colon. In our previous application entitled "Dual View Endoscope"; (application Ser. No. 10/711,859; dated Oct. 11. 2004), a colonoscope was presented with means to provide both forward and rear views during a single passage through the colon. In the present invention, we present a colonoscope with means to examine a given segment of the colon multiple times during a single passage through the colon. This is achieved by strategically adding multiple 'dual view modules' to the shaft of a conventional colonoscope. A 'dual view module' is a solid, tubular or inflatable structure containing a forward and a rear image lens; and a forward and a rear illumination bulb. The 'dual view module' can be of different shapes, sizes and configurations. It is attached to the shaft of the colonoscope using one of many available mechanical articulation mechanisms. Once deployed, the 'dual view module' positions the forward and rear image lens to view the corresponding colonic segment. In the present invention, we present a 'next generation colonoscope' that contains multiple 'dual view modules' placed along its shaft. The 'dual view modules' are strategically spaced apart from one another. Once the 'next generation colonoscope' reaches the desired end point, the 'dual view modules' are deployed. As the colonoscope is pulled out, a given segment of the colon is examined multiple times during a single passage through the colon; each time with a 'dual view module' distal to the previous 'dual view module'. Each 'dual view module' has a corresponding instrument and air/water channel located proximally; which services the 'dual view module'. The instrument channel enables surgical procedures to be performed seamlessly in an area under the field of view of the corresponding 'dual view modules'. An added advantage of the 'next generation colonoscope' is that, by virtue of a multiple instrument channels, it enables surgical procedures to be performed at the time a lesion is detected; without having the need to postpone it till such a time when an instrument channel is suitably positioned to access the said lesion. According to another aspect, the 'next generation colonoscope' enables removal of multiple polyps during a single passage through the colon.

These and other advantages; and the workings of the 'next generation colonoscope' are discussed in details in the description and drawings, which follow. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out one or several purposes of the present invention. It is important, therefore, that the claims be regarded as including such equivalent constructions insofar as they do not depart from the spirit and scope of the present invention. Additional features and advantages of the present invention will be set forth in the description and drawings which follow or may be learned by practice of the invention

BRIEF DESCRIPTION OF THE DRAWINGS

The drawings are illustrative embodiments. The drawings are not necessarily to scale and certain features may be removed, exaggerated, moved, or partially sectioned for clearer illustration. The embodiments illustrated herein are not intended to limit or restrict the claims.

FIG. 4B shows the control valve assembly of the instrument channel wherein the valves are in an open position.

FIG. 5A shows the control valve assembly of the air/water channel wherein the valve is in a closed position.

FIG. 22B is a view of the display unit displaying images from the 'next generation colonoscope' wherein the pictures from, image lenses of adjacent 'dual view modules' forming a 'view unit' have been converged.

FIG. 23A is a view of a conventional 'polyp retrieval assembly.

FIG. 23B shows removal of a large colonic polyp using a conventional 'polyp retrieval assembly' wherein the said polyp is grasped within the net.

FIG. 26A is an exploded view of a monitor connected to the colonoscope of FIG. 25.

FIG. 26B is an exploded view of a monitor connected to the colonoscope of FIG. 25, illustrating images in an embodiment of a consolidated view.

FIG. 27 is an enlarged view of portion A of FIG. 25, illustrating the colonoscope in a polyp removal configuration.

FIG. 28 is an exploded view of a monitor connected to the colonoscope of FIG. 27.

DETAILED DESCRIPTION

Reference will now be made in detail to the preferred embodiments of the invention, examples of which are illustrated in the accompanying drawings. Wherever possible, the same reference numbers will be used throughout the drawings to refer to the same or like parts. The following general description applies to preferred embodiments of the present invention.

Figure 1:
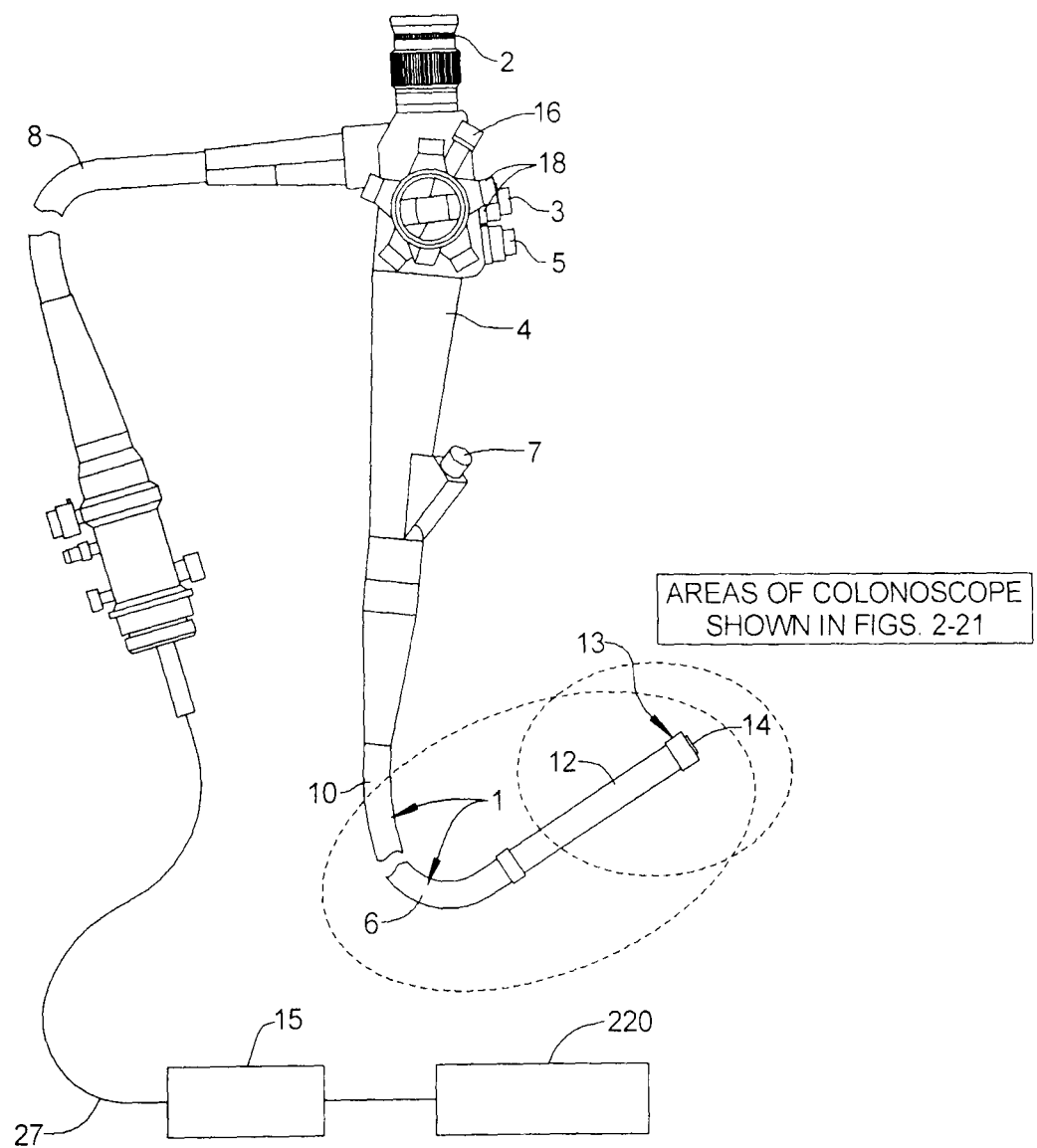
FIG. 1 is a general view of a conventional colonoscope including an exemplary embodiment of an image processor and a display.
Figure 2:
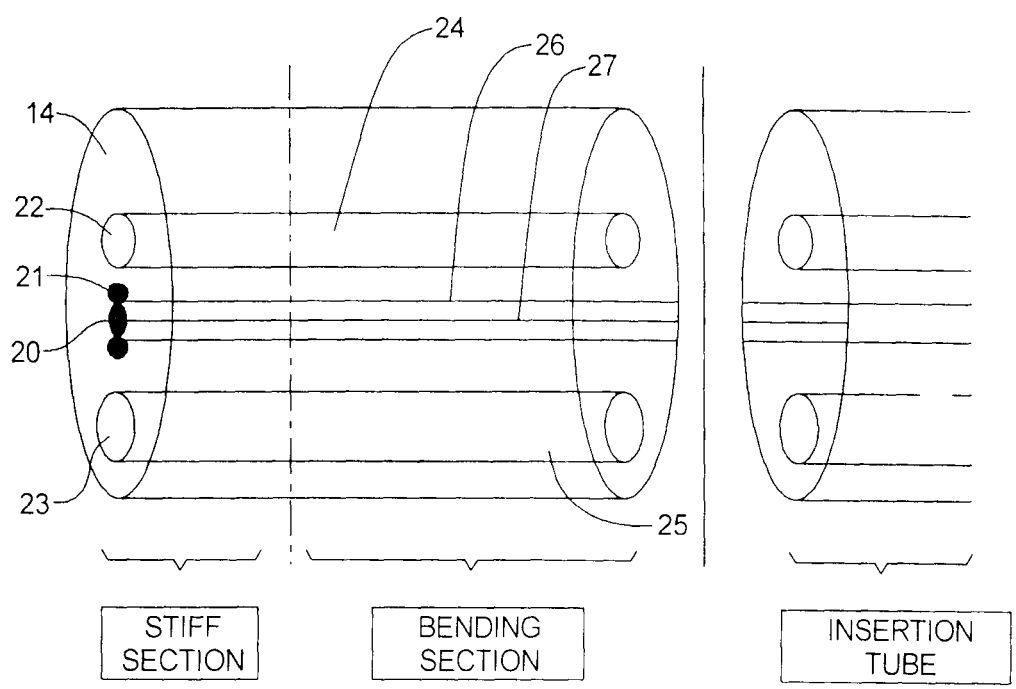
FIG. 2 shows a schematic representation of the side view of the inside of a conventional colonoscope.
Figure 3:
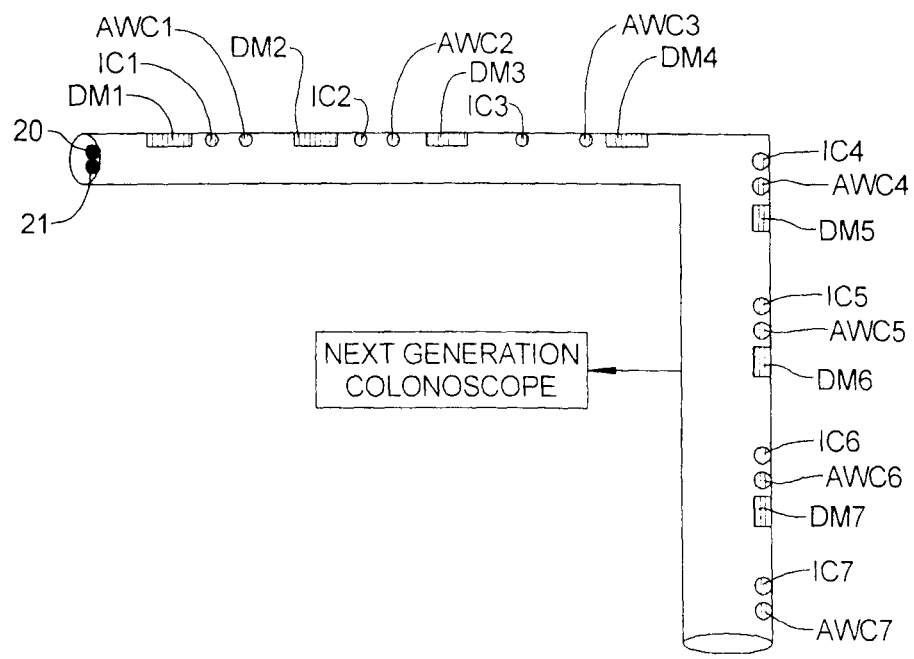
FIG. 3 shows an overall view of the 'next generation colonoscope'.

The basic unit of the present invention comprises of a 'dual view module' (DM); as shown in FIGS. 6-20. In general terms, the 'next generation colonoscope' comprises of multiple 'dual view modules' (DM) that are placed along the length of its shaft. In the preferred embodiment of the present invention, the 'next generation colonoscope' contains seven 'dual view modules' (DM1-DM7) as shown in FIG. 3. The 'dual view modules' (DM1-DM7) are strategically spaced apart from each other. The different possible make, configuration and design of the 'dual view modules' (DM) are shown in FIGS. 6-20. Generally speaking, each 'dual view module' (DM) consists of; 1) a rear image lens (103) to obtain a rear view; 2) a forward image lens (105) to obtain a forward view; 3) rear illumination bulb (104) to illuminate the area under the field of view of the rear image lens (103); and 4) forward illumination bulb (106) to illuminate the area under the field of view of the forward image lens (105). The rear image lens (103) and the forward image lens (105) are connected to an image processor (15) by an electric cable (107). This cable transmits the image obtained by the rear and forward image lens (103 & 105) to the image processor (15). After being processed, the image is then viewed on a computer monitor or any other display unit. The rear and forward illumination bulbs (104 & 106) are connected to a power source by an electric cable (108). The rear illumination bulb (104) illuminates the area under view of the rear image lens (103); and the forward illumination bulb (106) illuminates the area under view of the forward image lens (105). The 'dual view module' (DM) is deployed using an actuator located on the handle of the 'next generation colonoscope'. One or all 'dual view modules' (DM 1 -DM7) may be deployed using the said actuator.

Figure 4A:
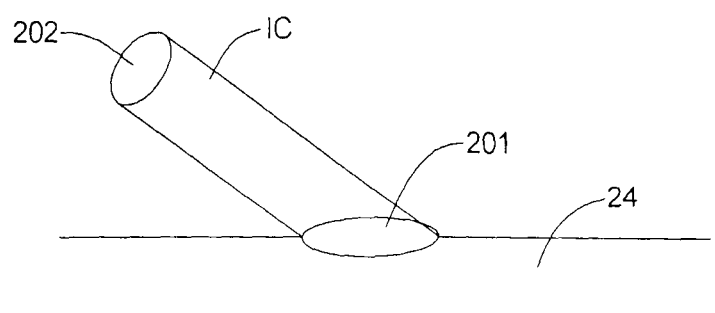
FIG. 4A shows the control valve assembly of the instrument channel wherein the valves are in a closed position.
Figure 5B:
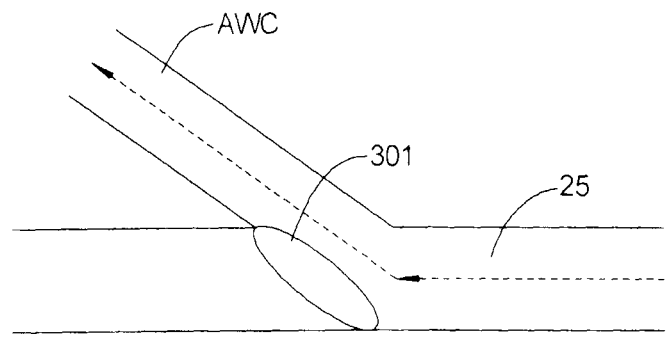
FIG. 5B shows the control valve assembly of the air/water channel wherein the valve is in an open position.

The 'next generation colonoscope' has a multitude instrument channels (IC1-IC7) and an air/water channels (AWC1-AWC7) that are located proximal to each 'dual view module' (DM1-DM7). In the preferred embodiment shown in FIG. 3, there are seven instrument channels (IC1-IC7) and seven air/water channels (AWC1-AWC7) located proximal to the corresponding 'dual view module' (DM1-DM7). It is also evident from FIG. 3 that the numbering pattern of the 'dual view modules' (DM1-DM7), instrument channels (IC1-IC7) and air/water channels (AWC1-AWC7) is similar in order to make the operation of the 'next generation colonoscope' user friendly. Each instrument channel (IC1-IC7) is connected to the main instrument channel (24). The passage from the main instrument channel (24) to the instrument channels (IC1-1C7) is controlled by a control valve assembly, which is shown in FIGS. 4A & 4B. The control valve assembly comprises to two valves, an inlet valve (201) and an outlet valve (202). FIG. 4A shows the valves (201 & 202) in the closed position and FIG. 4B shows the valves (201 & 202) in the open position. The instrument channel (IC1-IC7) is used to pass surgical instruments to do various surgical procedures in area under view of the corresponding 'dual view modules' (DM1-DM7). It is also used to apply suction in the area under view of the corresponding 'dual view modules' (DM1-DM7). Each air/water channel (AWC1-AWC7) is connected to the main air/water channel (25). The passage from the main air/water channel (25) to the air/water channel (AWC) is controlled by a control valve assembly, which is shown in FIGS. 5A & 5B. The control valve assembly comprises of an inlet valve (301) located at the air/water channel (AWC1-AWC7) inlet. FIG. 5A shows the valve (301) in the closed position and FIG. 5B shows the valve (301) in the open position. The air/water channel (AWC1-AWC7) is used to insufflate air in the area under the field of view of the corresponding 'dual view modules' (DM1-DM7) for better distension and visualization. The air/water channel (AWC1-AWC7) is also used to squirt water and/or air at the image lens (103 & 105) and illumination bulbs (104 & 106) of the corresponding 'dual view modules' (DM1-DM7). This enables cleaning of the image lens (103 & 105) and the illumination_bulbs (104 & 106); while the 'next generation colonoscope' is still inside the colon. The passage from the main instrument channel (24) into the instrument channels (IC1-IC7); and the passage from the main air/water channel (25) into the air/water channels (AWC1-AWC7) are controlled by actuators located on the handle (4). Using these actuators, any given instrument channel (IC1-IC7) and any given air/water channel (AWC1-AWC7) can be engaged. Once a said instrument channel (IC1-IC7) is engaged, any surgical instrument passed through the main instrument channel (24) is automatically guided into the said instrument channel (IC1-IC7). Similarly suction applied through the main instrument channel (24) is directed to the said engaged instrument channel (IC1-1C7). The same concept holds true for air/water channels (AWC1-AWC7). One an air/water channel (AWC1-AWC7) is engaged, the operations of the main air/water channel (25) is directed to the said air/water channel (AWC1-AWC7). The benefits of this arrangement are discussed in detail later in the manuscript.

The 'dual view module' (DM) can be of any suitable make, design and configuration. Now, we will discuss some embodiments of the 'dual view module' (DM) that may be used with the 'next generation colonoscope'. it is to be understood that in addition to the embodiments discussed henceforth; there may be other embodiments that could be used to achieve the purpose of the present invention. A particular embodiment of the 'dual view module' (DM) should not be considered limiting.

Figure 6A:
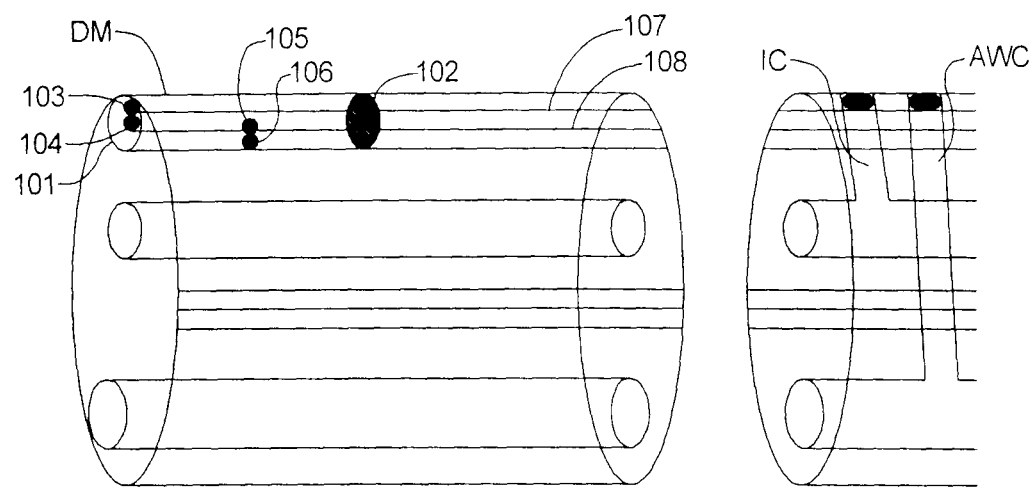
FIG. 6A is a side view of the first preferred embodiment of the 'dual view module'.
Figure 6B:
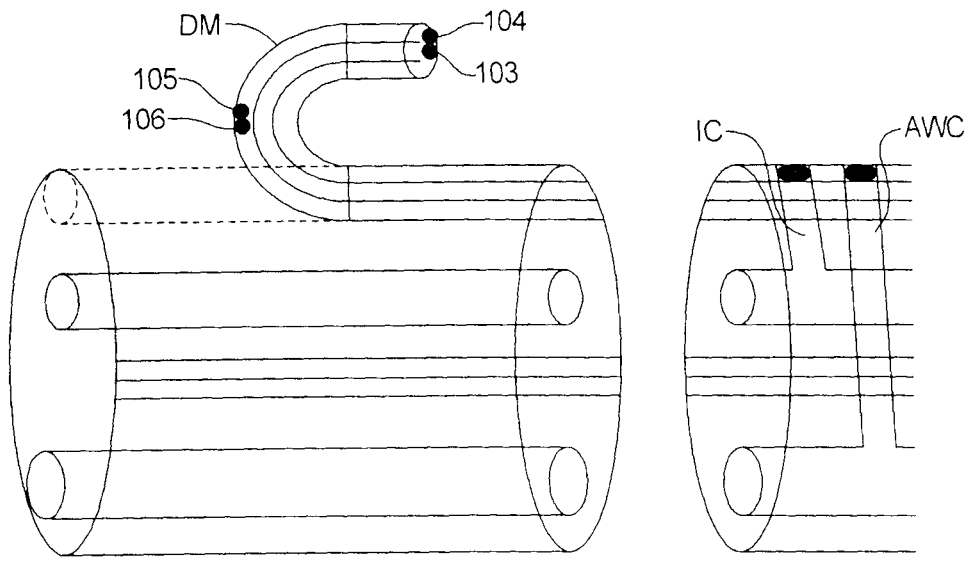
FIG. 6B is a side view of the first preferred embodiment of the 'dual view module' wherein the said 'dual view module' has been deployed.

FIGS. 6A & 6B show a side view of a first preferred embodiment of the 'dual view module' (DM). The 'dual view module' (DM) is a thin tubular structure encased in a sheath. It is placed along the longitudinal axis of the shaft of the 'next generation colonoscope'. The 'dual view module' (DM) has a distal end (101), stiff section and bending section. The proximal end (102) of 'dual view module' (DM) has a rear and forward image lens (103 & 105); and a rear and forward illumination bulb (104 & 106). The rear and forward image lens (103 & 105) are connected to an image processor (not shown) and the illumination bulbs (104 & 106) are connected to a power source (not shown) by electrical cables (107 & 108). Two pairs of cables within the 'dual view module' (DM) attach the bending section of the 'dual view module' (DM) to an actuator. Tension on these cables moves the bending section of the 'dual view module' (DM) in vertical and horizontal planes. FIG. 6B shows the 'dual view module' (DM) of FIG. 6A wherein; the 'dual view module' (DM) is retro flexed. With this maneuver, the rear image lens (103) faces backwards and provides a rear view; and the forward image lens (105) faces forwards and provides a forward view. The rear illumination bulb (104) illuminates the area under view of the rear image lens (103); and the forward illumination bulb (106) illuminates the area under the view of the forward image lens (105). Because the 'dual view module' (DM) is thin, retro flexion can be achieved with a small radius of curvature; and thus can be performed even inside a narrow hollow organ such as colon.

Figure 7A:
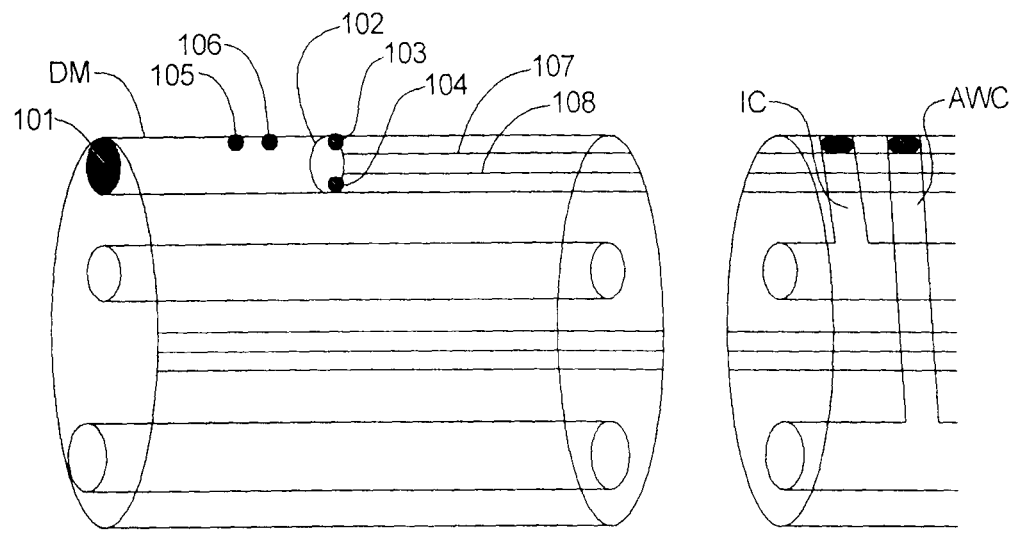
FIG. 7A is a side view of the second preferred embodiment of the 'dual view module'.
Figure 7B:
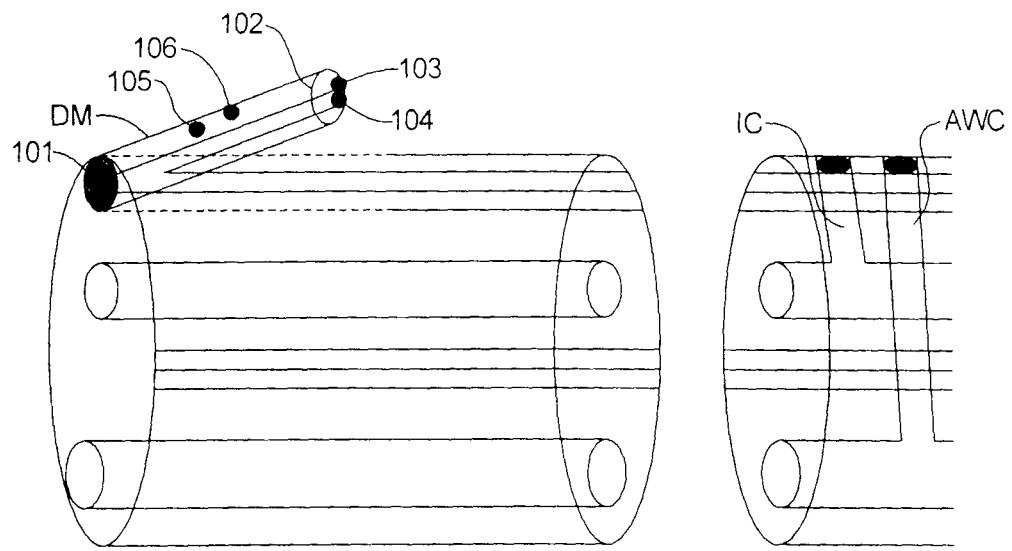
FIG. 7B is a side view of the second preferred embodiment of the 'dual view module' wherein the said 'dual view module' has been deployed.

FIGS. 7A & 7B show a side view of the second preferred embodiment of the 'dual view module' (DM). The 'dual view module' (DM) is a solid or tubular block with a proximal end (102) and a distal end (101). The rear image lens (103) and the rear illumination bulb (104) are located on the proximal end (102); and the forward image lens (105) and the forward illumination bulb (106) are located on the outer edge of the 'dual view module' (DM). The rear and forward image lens (103 & 105) are connected to an image processor and the rear and forward illumination bulbs (104 & 106) are connected to a power source by electric cables (107 & 108). The distal end (101) of the 'dual view module' (DM) is attached to the shaft of the 'next generation colonoscope' by a hinge joint or any other suitable mechanical articulation. The distal end (101) of the 'dual view module' (DM) is also connected to an actuator located on the handle of the 'next generation colonoscope' by a pair of cables (not shown). Tension on these cables moves the proximal end (102) of the 'dual view module' (DM) away from and towards the shaft of the 'next generation colonoscope', as shown in FIG. 7B. FIG. 7B is a side view of the 'dual view module (DM) of FIG. 7A wherein the 'dual view module' (DM) has been deployed by lifting its proximal end (102) away from the shaft using an actuator. When fully deployed, the rear image lens (103) and the rear illumination bulb (104) face backwards and give a rear view; and the forward image lens (105) and the forward illumination bulb (106) faces forwards and give a forward view. A major advantage of this embodiment of the 'dual view module' (DM) is that it requires only minimal additional space when deployed. This is of particular advantage when examining a narrow body cavity such as colon.

Figure 8A:
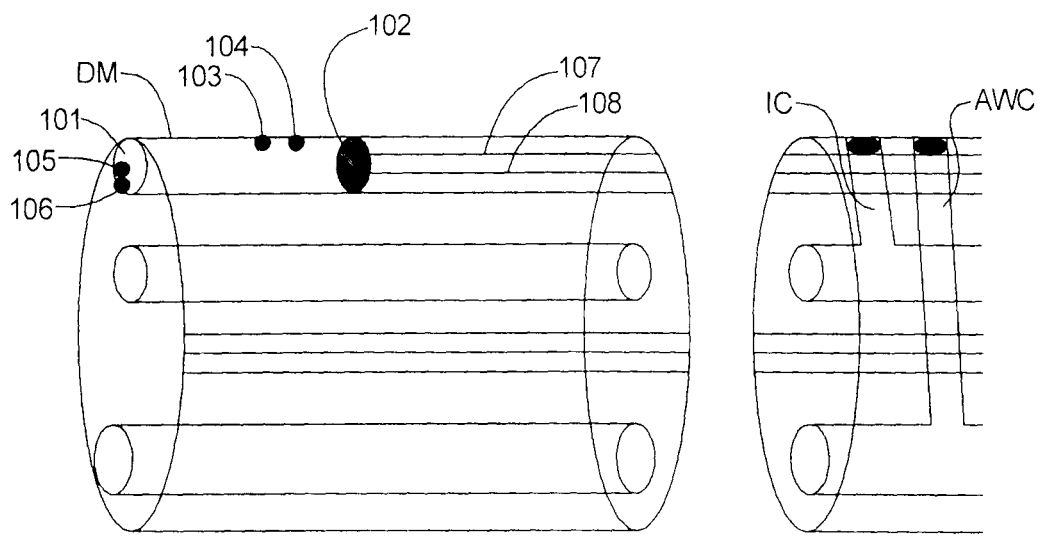
FIG. 8A is a side view of the third preferred embodiment of the 'dual view module'.
Figure 8B:
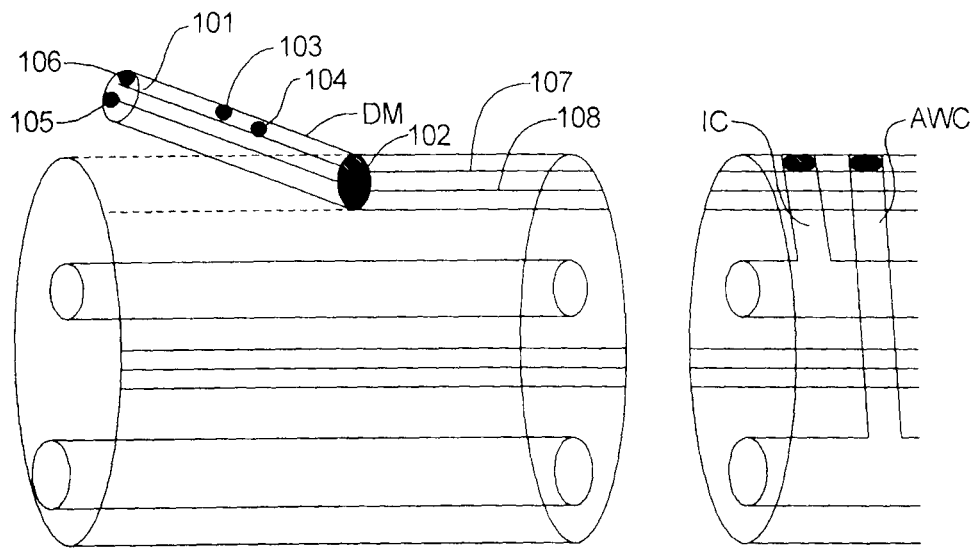
FIG. 8B is a side view of the third preferred embodiment of the 'dual view module' wherein the said 'dual view module' has been deployed.

FIGS. 8A & 8B show a side view of the third preferred embodiment of the 'dual view module' (DM). The 'dual view module' (DM) is a solid or tubular block with a proximal end (102) and a distal end (101). The rear image lens (103) and the rear illumination bulb (104) are located on the outer edge of the 'dual view module' (DM); and the forward image lens (105) and the forward illumination bulb (106) are located on the distal end (101) of the 'dual view module' (DM). The rear and forward image lens (103 & 105) are connected to an image processor and the rear and forward illumination bulbs (104 & 106) are connected to a power source by electric cables (107 & 108). The proximal end (102) of the 'dual view module' (DM) is attached to the shaft of the 'next generation colonoscope' by a hinge joint or any other suitable mechanical articulation. The proximal end (102) of the 'dual view module' (DM) is also connected to an actuator located on the handle of the 'next generation colonoscope' by a pair of cables (not shown). Tension on these cables moves the distal end (101) of the 'dual view module' (DM) away from and towards the shaft of the 'next generation colonoscope', as shown in FIG. 8B. FIG. 8B is a side view of the 'dual view module' (DM) of FIG. 8A wherein the 'dual view module' (DM) has been deployed by lifting its distal end (101) away from the shaft using an actuator. When fully deployed, the rear image lens (103) and the rear illumination bulb (104) face backwards and give a rear view; and the forward image lens (105) and the forward illumination bulb (106) faces forwards and give a forward view. A major advantage of this embodiment of the 'dual view module' (DM) is that it requires only minimal additional space when deployed. This is of particular advantage when examining a narrow body cavity such as colon.

Figure 9A:
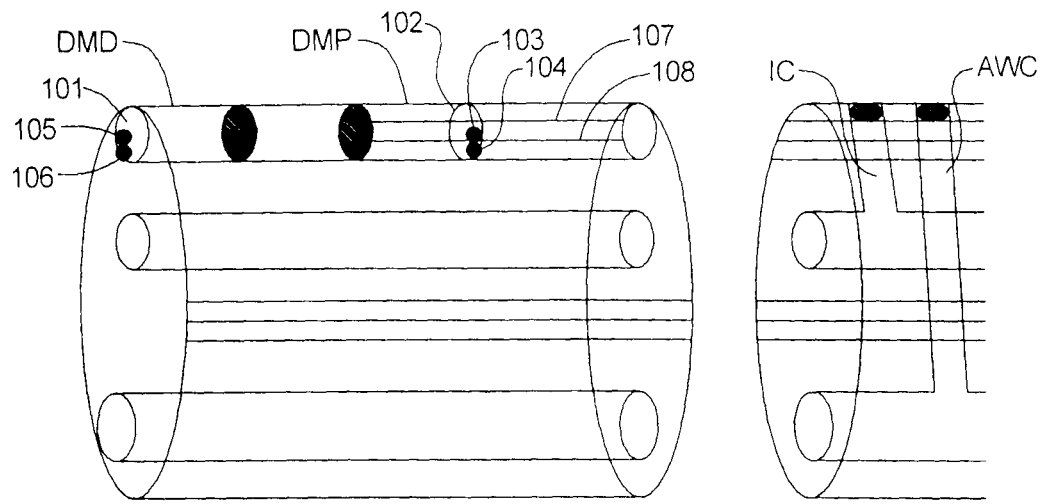
FIG. 9A is a side view of the fourth preferred embodiment of the 'dual view module'.
Figure 9B:
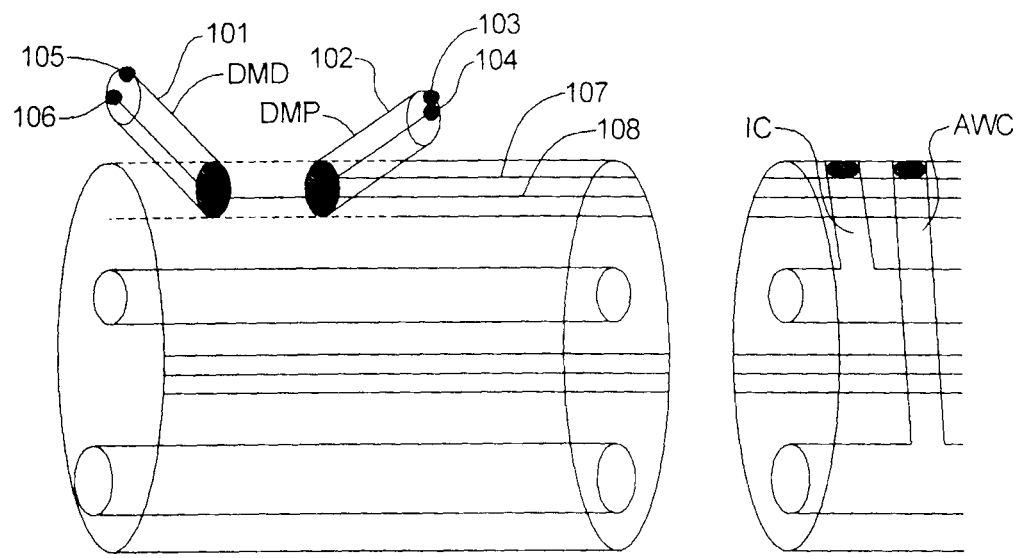
FIG. 9B is a side view of the fourth preferred embodiment of the 'dual view module' wherein the said 'dual view module' has been deployed.

FIGS. 9A & 9B show a side view of the fourth preferred embodiment of the 'dual view module' (DM). The 'dual view module' (DM) comprises of two solid or tubular blocks; proximal (DMP) and distal (DMD). The rear image lens (103) and the rear illumination bulb (104) are located on the proximal block (DMP); and the forward image lens (105) and the forward illumination bulb (106) are located on the distal block (DMD). The rear and forward image lens (103 & 105) are connected to an image processor by electric cable (107); and the rear and forward illumination bulbs (104 & 106) are connected to a power source by an electric cable (108). The blocks (DMP & DMD) are attached to the shaft of the 'next generation colonoscope' by a hinge joint or any other suitable mechanical articulation. The blocks (DMP & DMD) are also connected to an actuator located on the handle of the 'next generation colonoscope' by a pair of cables (not shown). Tension on these cables moves the rectangular blocks (DMP & DMD) away from and towards the shaft of the 'next generation colonoscope', as shown in FIG. 9B. FIG. 9B is a side view of the 'dual view module' (DM) of FIG. 9A wherein the 'dual view module' (DM) has been deployed by lifting the two rectangular blocks (DMP & DMD) away from the shaft using an actuator. When fully deployed, the rear image lens (103) and the rear illumination bulb (104); located on the proximal rectangular block (DMP); face backwards and give a rear view; and the forward image lens (105) and the forward illumination bulb (106); located on the distal rectangular block (DMD); faces forwards and give a forward view.

Figure 10A:
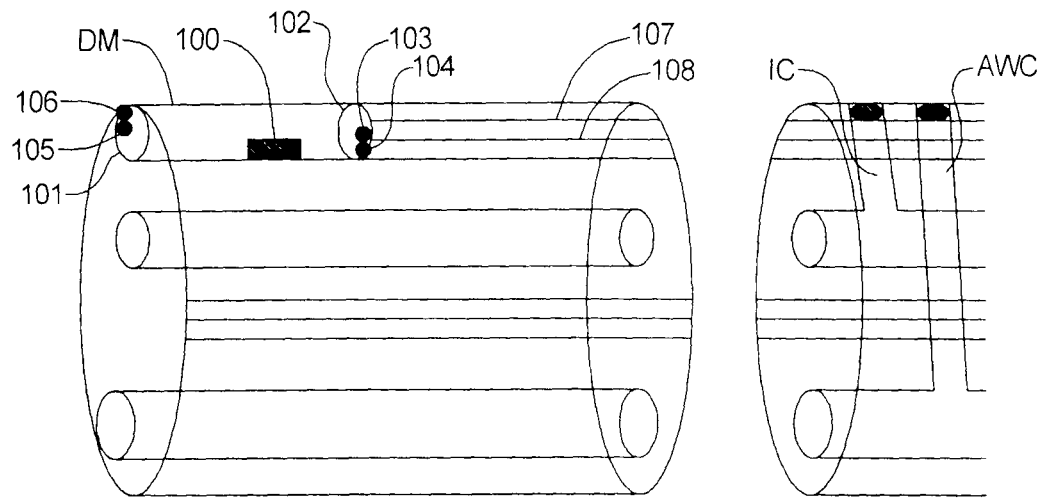
FIG. 10A is a side view of the fifth preferred embodiment of the 'dual view module'.
Figure 10B:
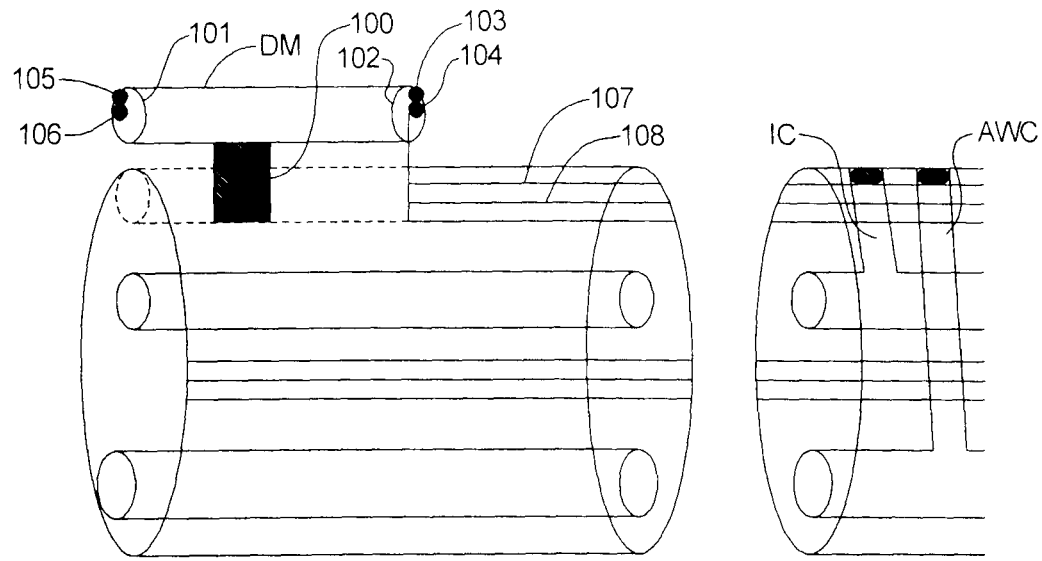
FIG. 10B is a side view of the fifth preferred embodiment of the 'dual view module' wherein the said 'dual view module' has been deployed.

FIGS. 10A & 10B show a side view of the fifth preferred embodiment of the 'dual view module' (DM). The 'dual view module' (DM) is a solid or tubular block with a proximal (102) and a distal end (101). The rear image lens (103) and the rear illumination bulb (104) are placed on the proximal end (102); and the forward image lens (105) and the forward illumination bulb (106) are placed on the distal end (101) of the 'dual view module' (DM). The rear and forward image lens (103 & 105) are connected to an image processor; and the rear and forward illumination bulbs (104 & 106) are connected to a power source by electric cables (107 & 108). The 'dual view module' (DM) rests on a support pillar/spring (100). The support pillar/spring (100) is attached to an actuator by cables; and can be extended and retracted perpendicular to the shaft of the 'next generation colonoscope'. FIG. 10B shows the 'dual view module' (DM) of FIG. 10A wherein it has been deployed by moving the support pillar/spring vertically, away from the shaft using the actuator. In this position, the rear image lens (103) and the rear illumination bulb (104) face backwards and provide a rear view; whereas the forward image lens (105) and the forward illumination bulb (106) faces forward and provide a forward view. A major advantage of this embodiment of the 'dual view module' (DM) is that it provides a straight rear and forward view that may be desirable for certain surgical procedures.

Figure 11A:
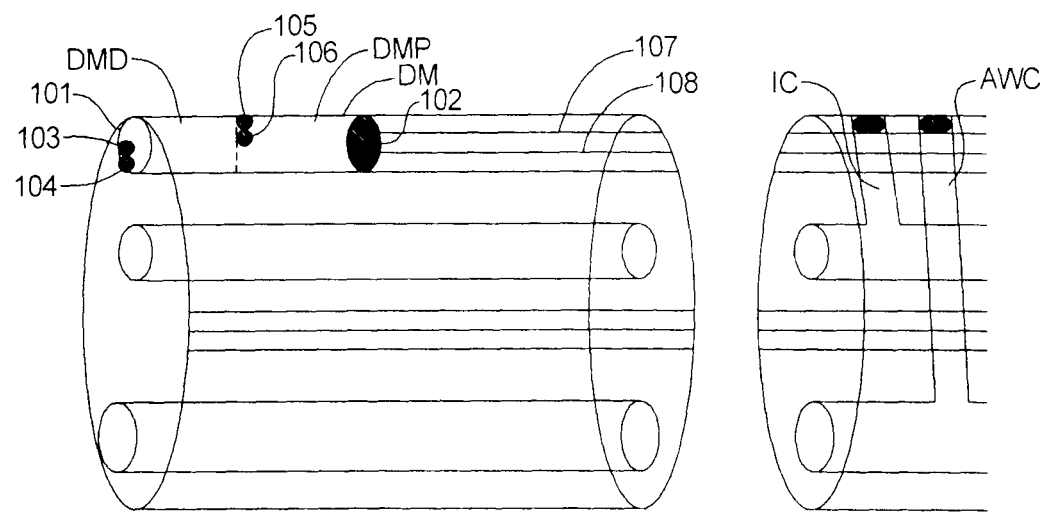
FIG. 11A is a side view of the sixth preferred embodiment of the 'dual view module'.
Figure 11B:
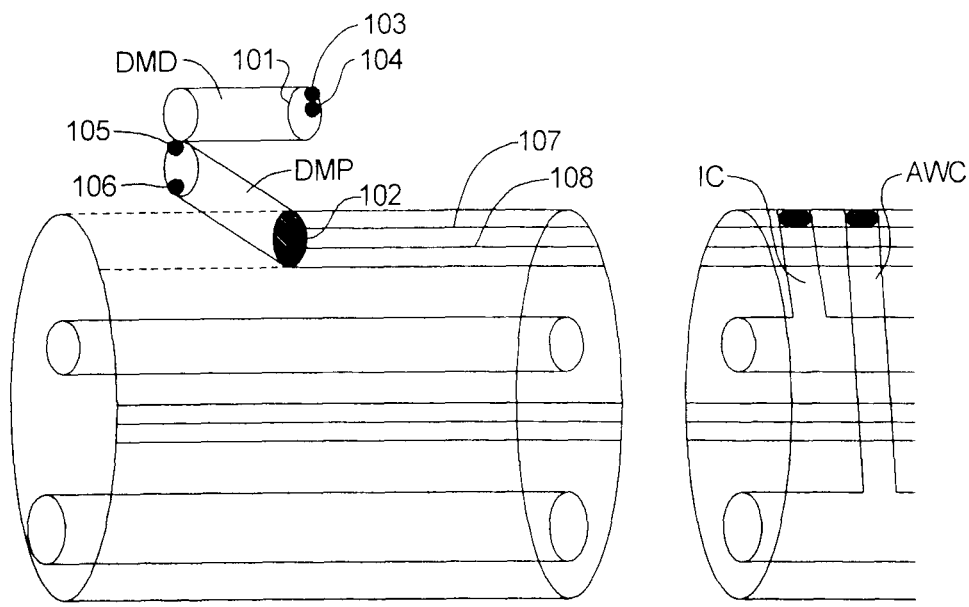
FIG. 11B is a side view of the sixth preferred embodiment of the 'dual view module' wherein the said 'dual view module' has been deployed.

FIGS. 11A & 11B show a side view of the sixth preferred embodiment of the 'dual view module' (DM). The 'dual view module' (DM) comprised of two solid or tubular blocks; a proximal block (DMP) and a distal block (DMD); that are attached together by a hinge joint or any other suitable mechanical articulation. The rear image lens (103) and the rear illumination bulb (104) are placed on the distal end (101) of the distal block (DMD); and the forward image lens (105) and the forward illumination bulb (106) are placed on the distal end of the proximal block (DMP). The rear and forward image lens (103 & 105) are connected to an image processor; and the rear and forward illumination bulbs (104 & 106) are connected to a power source by electric cables (107 & 108). The proximal end of the proximal block (DMP) is attached to the shaft of the 'next generation colonoscope' by means of a hinge joint or any other suitable mechanical articulation. The blocks (DMP & DMD) are attached to an actuator by cables; and can be deployed and retracted. FIG. 11B shows the 'dual view module' (DM) of FIG. 11A wherein it has been deployed by moving the 'dual view module'. (DM) away from the shaft; and thereafter flipping the distal block (DMD) backwards. In this position, the rear image lens (103) and the rear illumination bulb (104) face backwards and provide a rear view; whereas the forward image lens (105) and the forward illumination bulb (106) faces forward and provide a forward view.

Figure 12A:
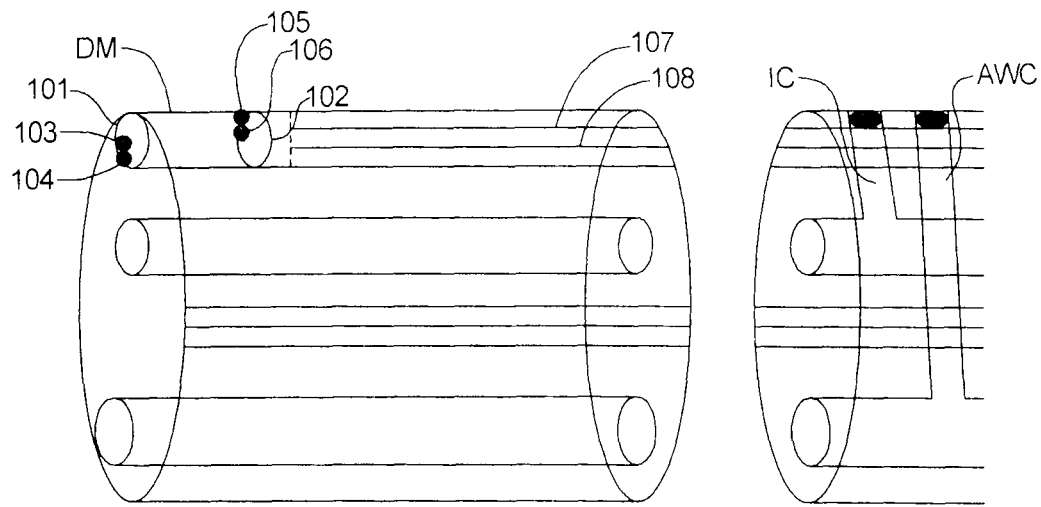
FIG. 12A is a side view of the seventh preferred embodiment of the 'dual view module'.
Figure 12B:
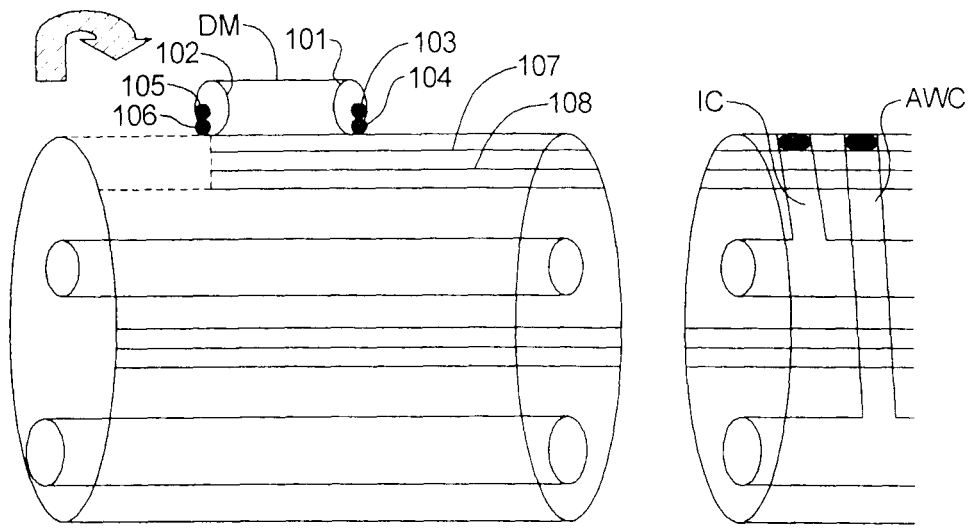
FIG. 12B is a side view of the seventh preferred embodiment of the 'dual view module' wherein the said 'dual view module' has been deployed.

FIGS. 12A & 12B show a side view of the seventh preferred embodiment of the 'dual view module' (DM). The 'dual view module' (DM) is a solid or tubular block placed within the shaft of the 'next generation colonoscope'. The proximal end (102) is attached to the shaft my means of a hinge joint or any other suitable mechanical articulation. The rear image lens (103) and the rear illumination bulb (104) are placed on the distal end (101); and the forward image lens (105) and the forward illumination bulb (106) are placed on the proximal end (102) of the 'dual view module' (DM). The rear and forward image lens (103 & 105) are connected to an image processor; and the rear and forward illumination bulbs (104 & 106) are connected to a power source by electric cables (107 & 108)). The proximal end (102) of the 'dual view module' (DM) is connected to an actuator with the help of two cables, one on the outer edge and one on the inner edge. Tension on these cables deploys and retracts the 'dual view module' (DM) respectively; by flipping it upside down to 180 as shown in FIG. 12B; wherein the 'dual view module' (DM) is in a deployed position. In this position, the rear image lens (103) and the rear illumination bulb (104) face backwards and provide a rear view; whereas the forward image lens (105) and the forward illumination bulb (106) faces forward and provide a forward view. Again, a major advantage of this embodiment of the 'dual view module' (DM) is that it provides a straight rear and forward view that may be desirable for certain surgical procedures.

Figure 13A:
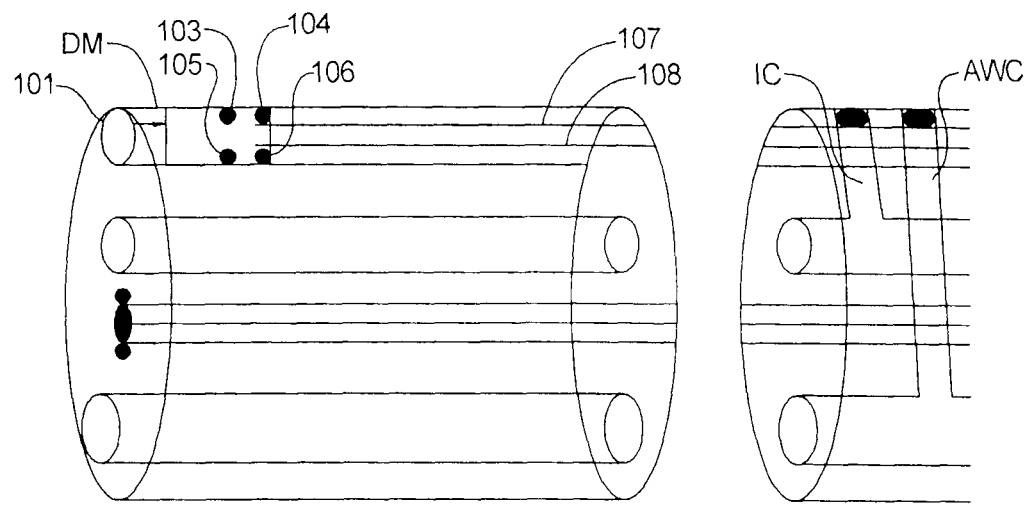
FIG. 13A is a side view of the eighth preferred embodiment of the 'dual view module'.
Figure 13B:
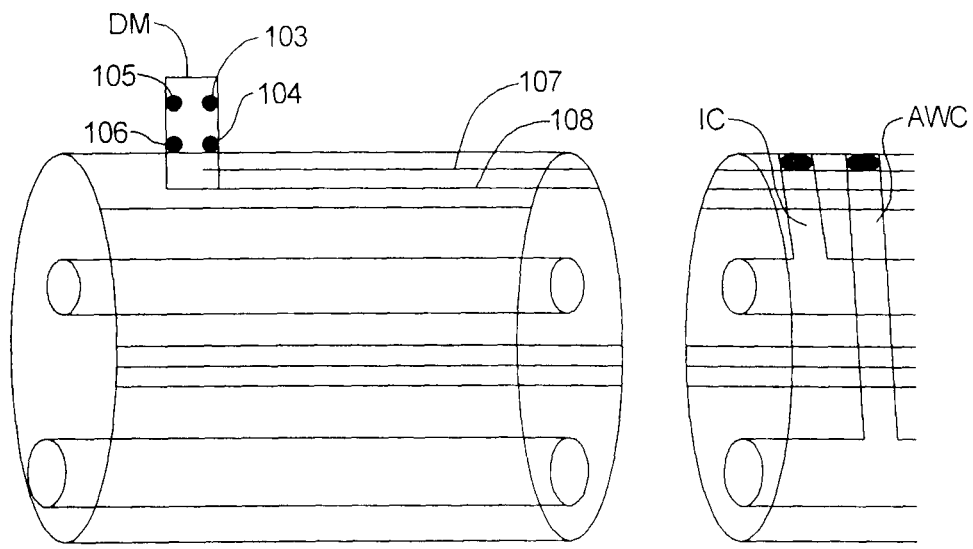
FIG. 13B is a side view of the eighth preferred embodiment of the 'dual view module' wherein the said 'dual view module' has been deployed.

FIGS. 13A & 13B show a side view of the eighth preferred embodiment of the 'dual view module' (DM). The 'dual view module' (DM) is a solid rectangular or tubular block placed within the shaft of the 'next generation colonoscope'. The distal end (101) of the 'dual view module' (DM) is attached to the shaft by means of a hinge joint or any other suitable mechanical articulation. The rear image lens (103) and the rear illumination bulb (104) are placed on the inner edge; and the forward image lens (105) and the forward illumination bulb (106) are placed on the outer edge of the 'dual view module' (DM) The rear and forward image lens (103 & 105) are connected to an image processor; and the rear and forward illumination bulbs (104 & 106) are connected to a power source by electric cable (107 & 108). The distal end (101) of the 'dual view module' (DM) is connected to an actuator with the help of two cables, one on its outer edge and one on the inner edge. Tension on these cables deploys and closes the 'dual view module' (DM) respectively. FIG. 13B shows the 'dual view module' (DM) of FIG. 13A wherein it has been deployed. In this position, the rear image lens (103) and the rear illumination bulb (104) face backwards and provide a rear view; whereas the forward image lens (105) and the forward illumination bulb (106) faces forward and provide a forward view. Again, a major advantage of this embodiment of the 'dual view module' (DM) is that it provides a straight rear and forward view that may be desirable for certain surgical procedures.

Figure 14A:
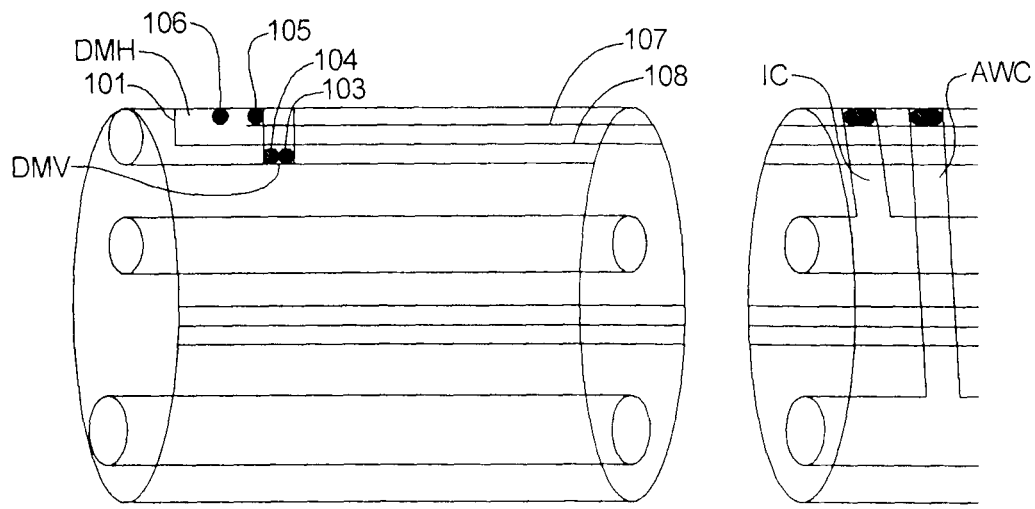
FIG. 14A is a side view of the ninth preferred embodiment of the 'dual view module'.
Figure 14B:
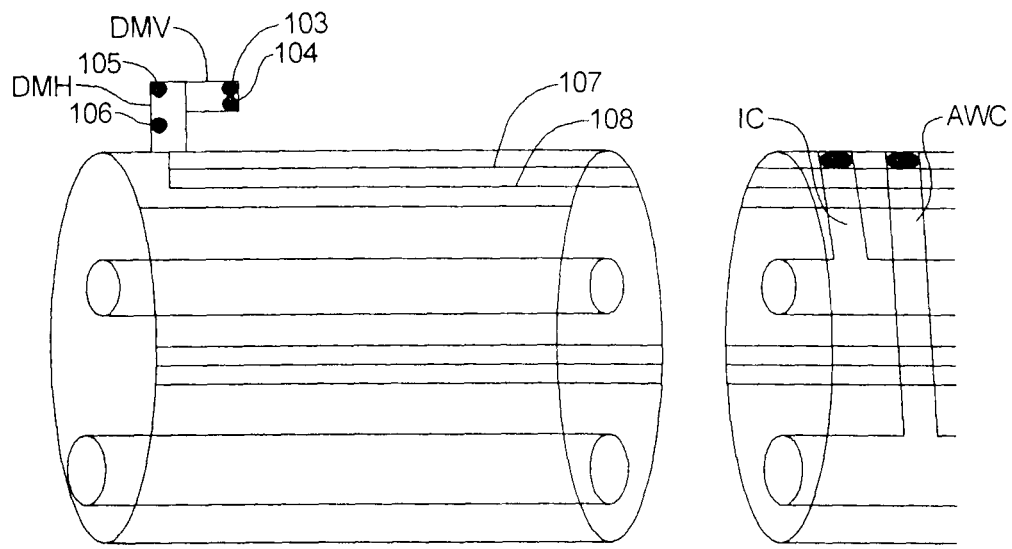
FIG. 14B is a side view of the ninth preferred embodiment of the 'dual view module' wherein the said 'dual view module' has been deployed.

FIGS. 14A & 14B show a side view of a ninth preferred embodiment of the 'dual view module' (DM). The 'dual view module' (DM) is a 'L' shaped solid or tubular structure. It is placed within the shaft of the 'next generation colonoscope', parallel to its long axis. The distal end (101) of the horizontal limb (DMH) of the 'dual view module' (DM) is connected to the shaft of the 'next generation colonoscope' by a hinge joint or any other suitable mechanical articulation. The rear image lens (103) and the rear illumination bulb (104) are placed on the vertical limb (DMV) of the 'dual view module' (DM); whereas the forward image lens (105) and the forward illumination bulb (106) are placed on the horizontal limb (DMH). The rear image lens (103) and the forward image lens (105) are connected to an image processor; and the rear illumination bulb (104) and the forward illumination bulb (106) are connected to a power source by electric cables (107 & 108). Two pairs of cables connect the distal end (101) of the horizontal limb (DMH) of the 'dual view module' (DM) to an actuator. Tension on these cables deploys and closes the 'dual view module' (DM) as shown in FIG. 14B. When deployed, the rear image lens (103) and the rear illumination bulb (104) face backwards; and the forward image lens (105) and the forward illumination bulb (106) face forwards. The rear image lens (103) gives a rear view and the rear illumination bulb (104) illuminates the area under view of the rear image lens (103). Similarly, the forward image lens (105) gives a forward view and the forward illumination bulb (106) illuminates the area under view of the forward image lens (105).

Figure 15A:
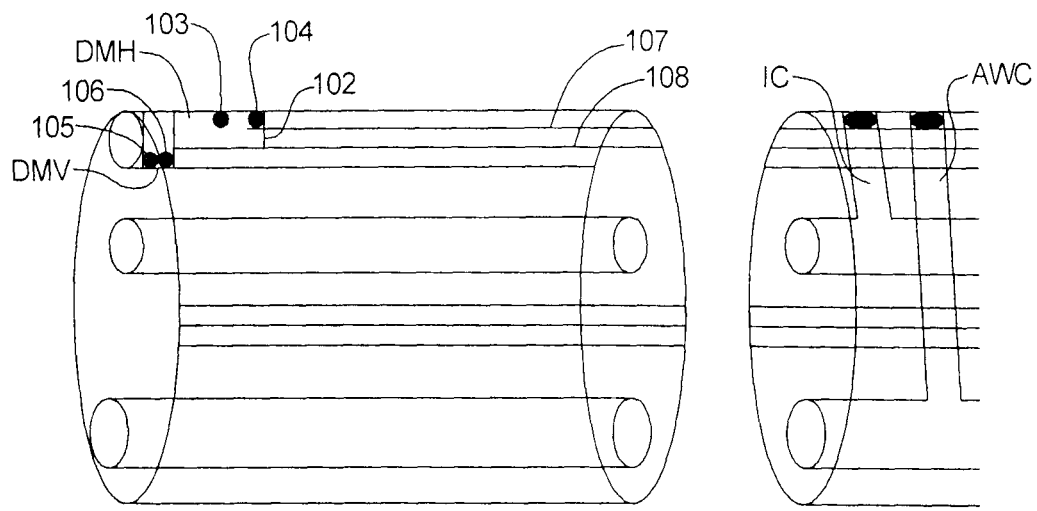
FIG. 15A is a side view of the tenth preferred embodiment of the 'dual view module'.
Figure 15B:
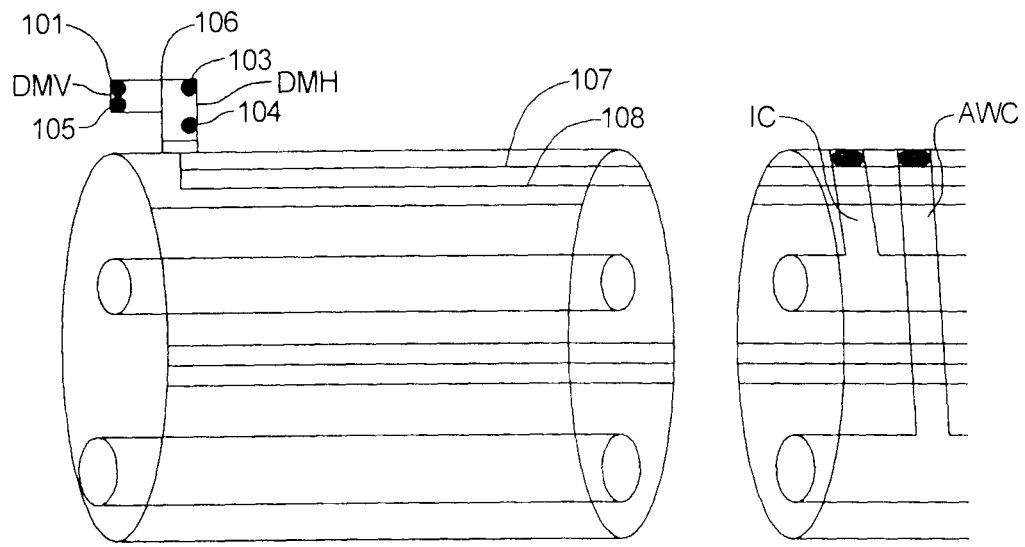
FIG. 15B is a side view of the tenth preferred embodiment of the 'dual view module' wherein the said 'dual view module' has been deployed.

FIGS. 15A & 15B show a side view of a tenth preferred embodiment of the 'dual view module' (DM). The 'dual view module' (DM) is an 'L' shaped solid or tubular structure. It is placed within the shaft of the 'next generation colonoscope', parallel to its long axis. The proximal end (102) of the horizontal limb (DMH) is connected to the shaft of the 'next generation colonoscope' by a hinge joint or any other suitable mechanical articulation. The rear image lens (103) and the rear illumination bulb (104) are placed on the horizontal limb (DMH) of the 'dual view module' (DM); whereas the forward image lens (105) and the forward illumination bulb (106) are placed on the vertical limb (DMV). The rear image lens (103) and the forward image lens (105) are connected to an image processor; and the rear illumination bulb (104) and the forward illumination bulb (106) are connected to a power source by electric cables (107 & 108). Two pairs of cables connect the proximal end (102) of the horizontal limb (DMH) of the 'dual view module' (DM) to an actuator. Tension on these cables deploys and closes the 'dual view module' (DM) as shown in FIG. 15B. When deployed, the rear image lens (103) and the rear illumination bulb (104) face backwards; and the forward image lens (105) and the forward illumination bulb (106) face forwards. The rear image lens (103) gives a rear view and the rear illumination bulb (104) illuminates the area under view of the rear image lens (103). Similarly, the forward image lens (105) gives a forward view and the forward illumination bulb (106) illuminates the area under view of the forward image lens (105).

Figure 16A:
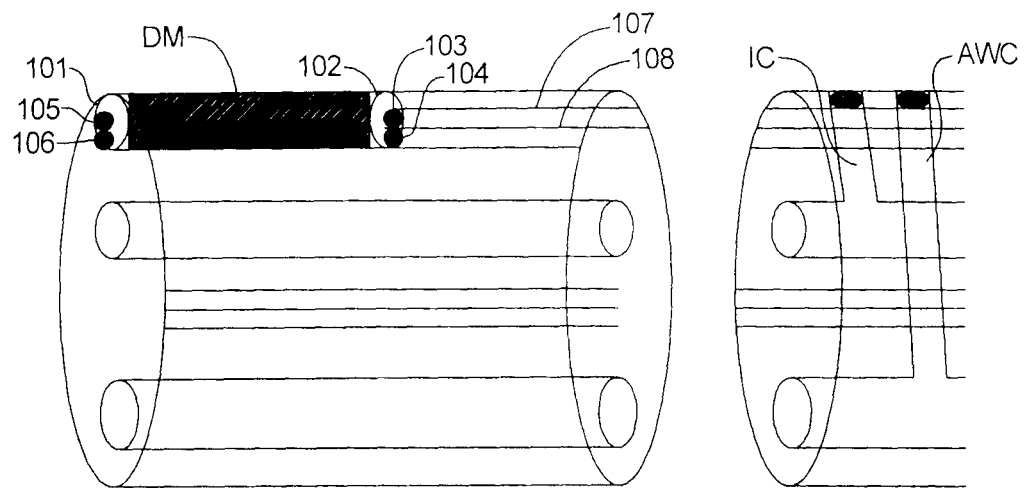
FIG. 16A is a side view of the eleventh preferred embodiment of the 'dual view module'.
Figure 16B:
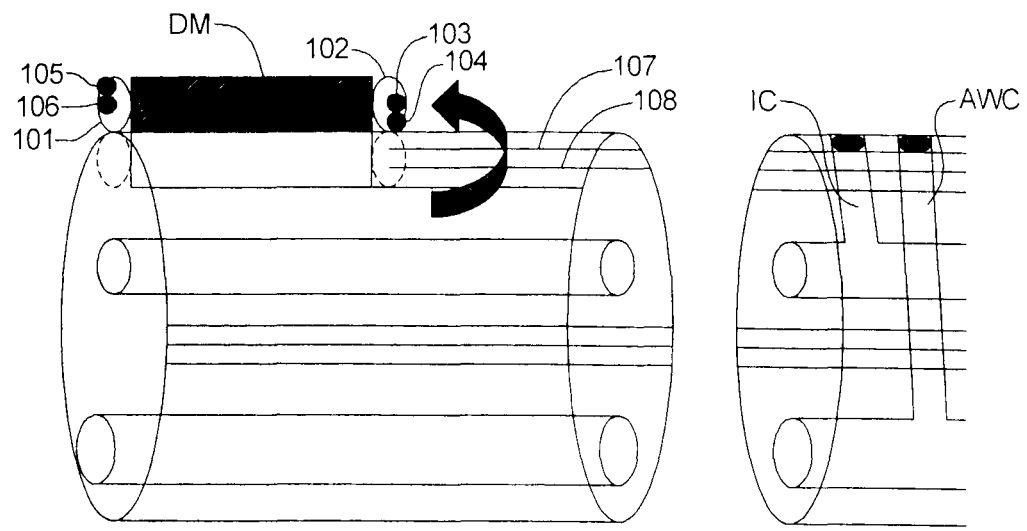
FIG. 16B is a side view of the eleventh preferred embodiment of the 'dual view module' wherein the said 'dual view module' has been deployed.

FIGS. 16A & 16B show a side view of the eleventh preferred embodiment of the 'dual view module' (DM). The 'dual view module' (DM) is a solid or tubular structure with a proximal end (102) and a distal end (101). It is placed within the shaft of the 'next generation colonoscope', parallel to its long axis. The 'dual view module' (DM) is connected along its length to the shaft of the 'next generation colonoscope' by a hinge joint or any other suitable mechanical articulation. The rear image lens (103) and the rear illumination bulb (104) are placed on the proximal end (102) whereas the forward image lens (105) and the forward illumination bulb (106) are placed on the distal end (101). The rear image lens (103) and the forward image lens (105) are connected to an image processor; and the rear illumination bulb (104) and the forward illumination bulb (106) are connected to a power source by electric cables (107 & 108). Two pairs of cables one on the outside and the other on the inside, connect the 'dual view module' (DM) to an actuator along its length. Tension on these cables opens and closes the 'dual view module' (DM) like the lid of a box; as shown in FIG. 16B. When deployed, the rear image lens (103) and the rear illumination bulb (104) face backwards; and the forward image lens (105) and the forward illumination bulb (106) face forwards. The rear image lens (103) gives a rear view and the rear illumination bulb (104) illuminates the area under view of the rear image lens (103). Similarly, the forward image lens (105) gives a forward view and the forward illumination bulb (106) illuminates the area under view of the forward image lens (105).

Figure 17A:
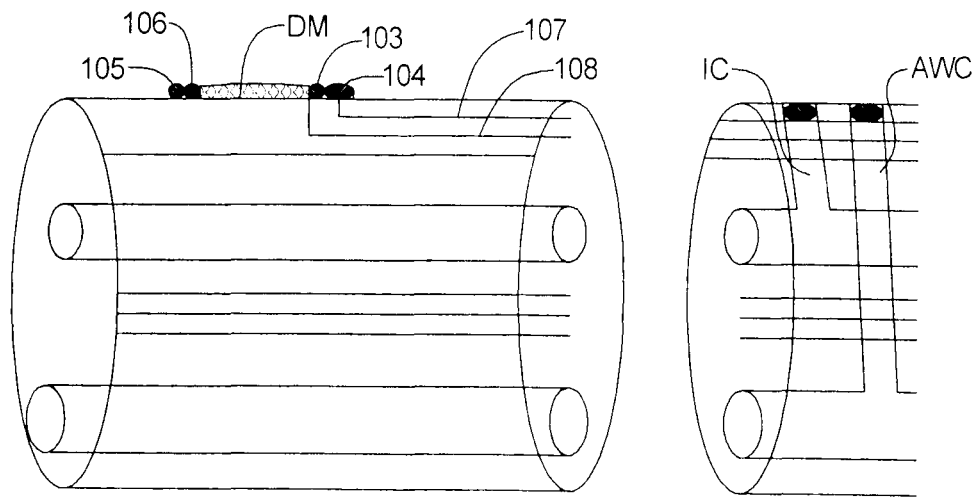
FIG. 17A is a side view of the twelfth preferred embodiment of the 'dual view module'.
Figure 17B:
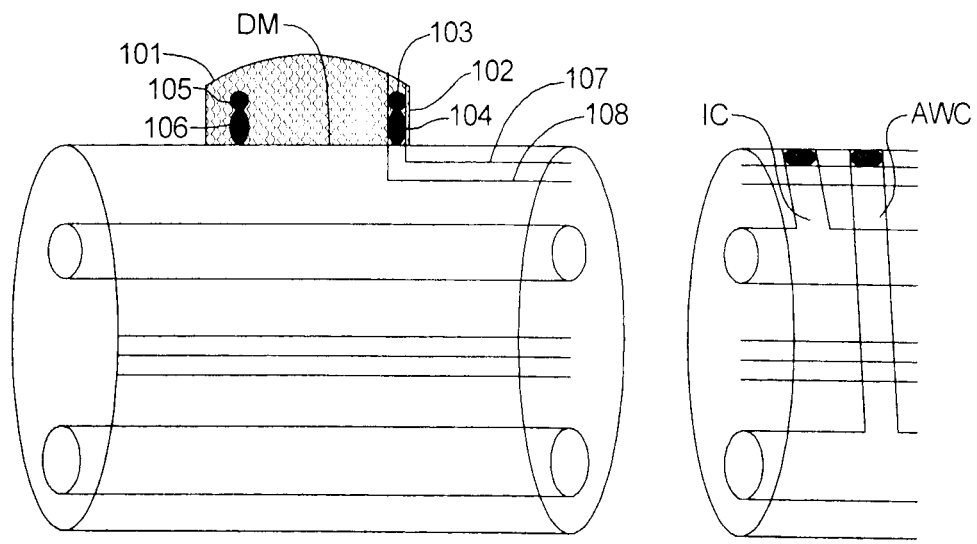
FIG. 17B is a side view of the twelfth preferred embodiment of the 'dual view module' wherein the said 'dual view module' has been deployed.

FIGS. 17A & 17B show a side view of the twelfth preferred embodiment of the 'dual view module' (DM). The 'dual view module' (DM) consists of an inflatable balloon or any other inflatable device that is attached along the length of the shaft of the 'next generation colonoscope'. The balloon is connected to an air pump by a thin tube placed within the shaft of the 'next generation colonoscope' (not shown). When inflated, the balloon has a proximal face (102) and a distal face (101) as shown in FIG. 17B. The proximal face (102) of the balloon contains the rear image lens (103) and the rear illumination bulb (104); and the distal face (101) of the balloon contains the forward image lens (105) and the forward illumination bulb (106). Electrical cables (107 & 108) connect the rear and forward image lens (103 & 105) to an image processor; and the rear illumination bulb (104) and the forward illumination bulb (106) to a power source. Inflating the balloon deploys the 'dual view module' (DM) as shown in FIG. 17B. When the balloon is fully inflated, the rear image lens (103) and the rear illumination bulb (104) face backwards and give a rear view. Similarly, the forward image lens (105) and the forward illumination bulb (106) face forwards and give a forward view.

Figure 18A:
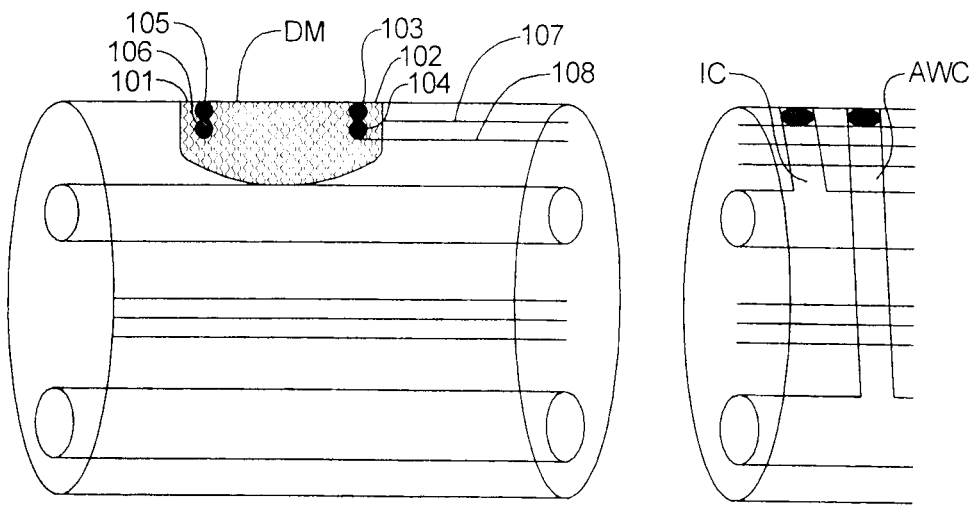
FIG. 18A is a side view of the thirteenth preferred embodiment of the 'dual view module'.
Figure 18B:
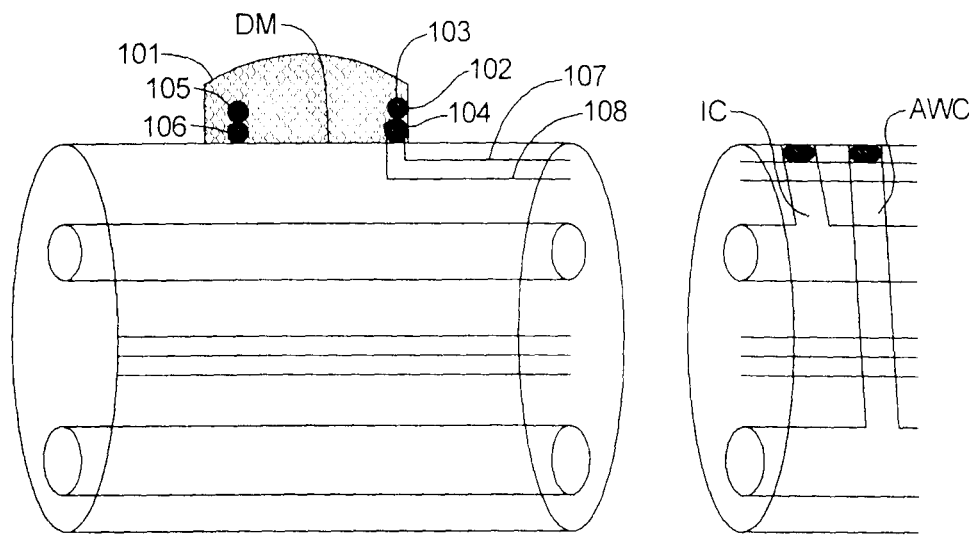
FIG. 18B is a side view of the thirteenth preferred embodiment of the 'dual view module' wherein the said 'dual view module' has been deployed.

FIGS. 18A & 18B show a side view of the thirteenth preferred embodiment of the 'dual view module' (DM). The 'dual view module' (DM) consists of a solid hemisphere. It is attached perpendicular to the long axis of the shaft of the 'next generation colonoscope'. The proximal face (102) of the hemisphere contains the rear image lens (103) and the rear illumination bulb (104); and the distal face (101) of the hemisphere contains the forward image lens (105) and the forward illumination bulb (106). Electrical cables (107 & 108) connect the rear and forward image lens (103 & 105) to an image processor; and the rear illumination bulb (104) and the forward illumination bulb (106) to a power source. The 'dual view module' (DM) is deployed by flipping it 180 degrees (mirror image), as shown in FIG. 18B. When the hemisphere is flipped 180 degrees, the rear image lens (103) and the rear illumination bulb (104) face backwards and give a rear view; and the forward image lens (105) and the forward illumination bulb (106) faces forwards and gives a forward view.

Figure 19A:
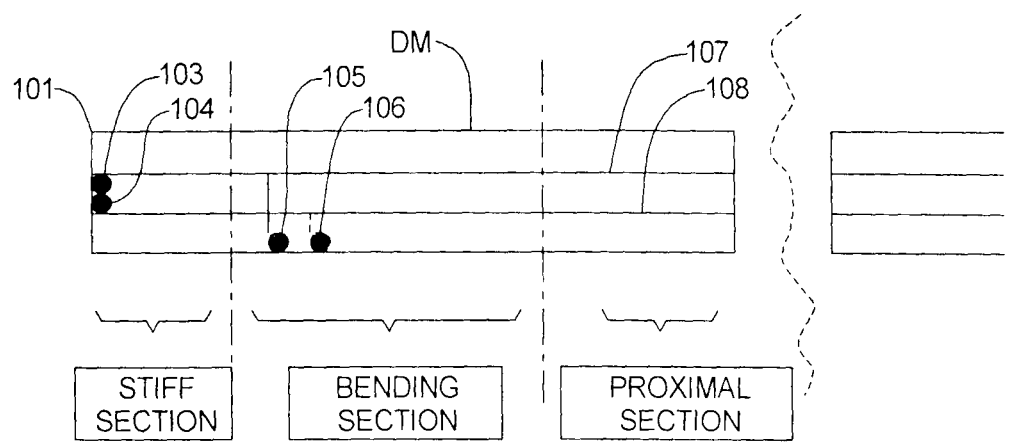
FIG. 19A is a side view of the fourteenth preferred embodiment of the 'dual view module'.
Figure 19B:
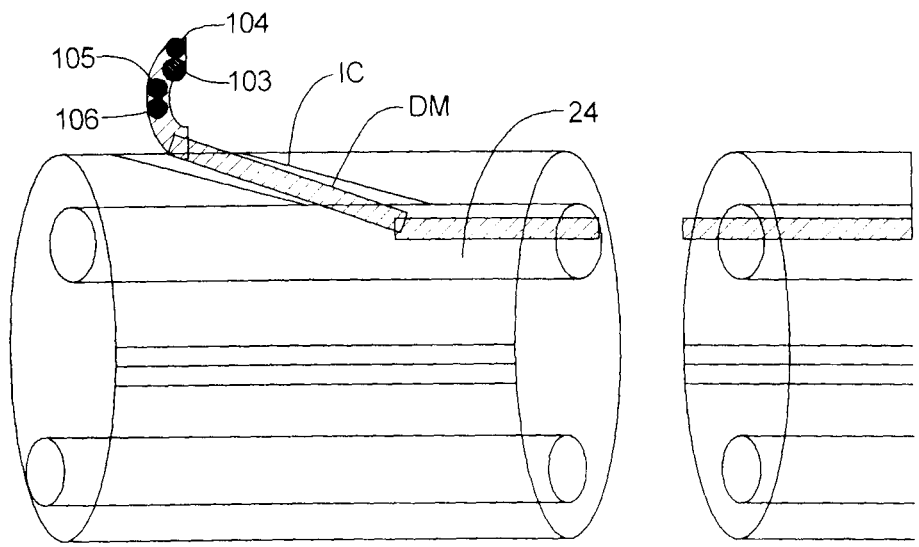
FIG. 19B is a side view of the fourteenth preferred embodiment of the 'dual view module' wherein the said 'dual view module' has been deployed.

FIGS. 19A & 19B show the fourteenth preferred embodiment of the 'dual view module' (DM). The 'dual view module' (DM) is a long and thin tubular structure encased in a sheath. It has a shaft that comprises of a distal end (101), stiff section, bending section and proximal section. The shaft is attached proximally to a handle (not shown). The handle has an extension that connects the 'dual view module' (DM) to an image processor and a power source. The rear image lens (103) and rear illumination bulb (104) are placed on the distal end (101). whereas the forward image lens (105) and the forward illumination bulb (106) are placed along the inner edge of the 'dual view module' (DM). The rear and forward image lens (103 & 105) and the rear and forward illumination bulbs (105 & 106) are connected to an image processor and a power source respectively by electrical cables (107 & 108). The bending section of the 'dual view module' is connected to an actuator by cables. Tension on these cables moves the bending section in vertical and horizontal planes. This entire assembly is thin enough to pass through the main instrument channel (24) of the endoscope. FIG. 19B shows the deployment of the 'dual view module' of FIG. 19A. The 'dual view module' (DM) is passed through the main instrument channel (24) into the corresponding instrument channel (IC) of the said 'dual view module' (DM). Dual view is obtained by retro flexing the 'dual view module' (DM) as shown in FIG. 19B. In this position, the rear image lens (103) and the rear illumination bulb (104) face backward and the forward image lens (105) and the forward illumination bulb (106) face forwards. The rear image lens (103) gives a rear view and the rear illumination bulb (104) illuminates the area under the view of the rear image lens (103). Similarly, the forward'image lens (105) gives a forward view and the forward illumination bulb (106) illuminates the area under the view of the forward image lens (105). It is evident from the discussion above that in order for this embodiment of the 'dual view module' (DM) to work with the 'next generation colonoscope'; the main instrument channel (24) will have to be wide enough to accommodate multiple such 'dual view modules' (DM).

Figure 20:
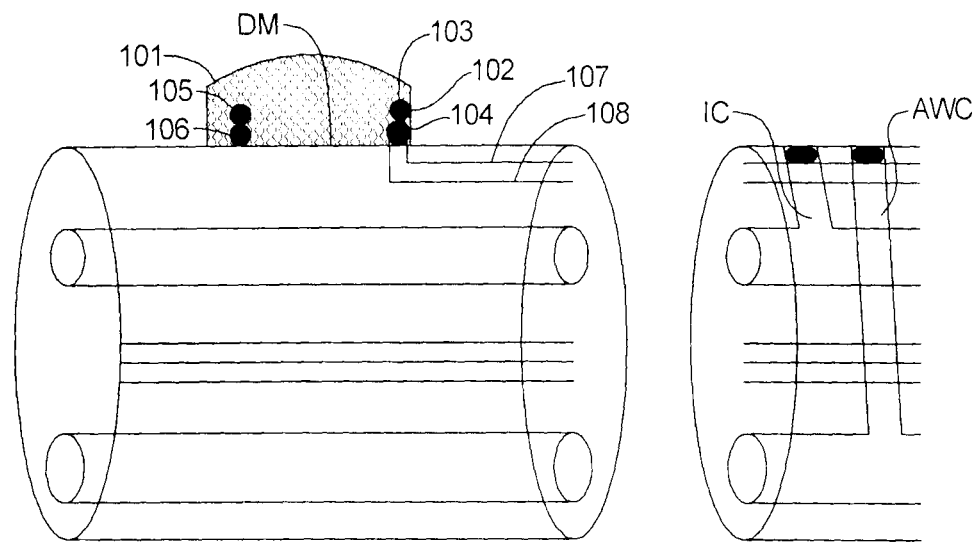
FIG. 20 is a side view of the fifteenth preferred embodiment of the 'dual view module', wherein the 'dual view module' is non retractable.
Figure 21A:
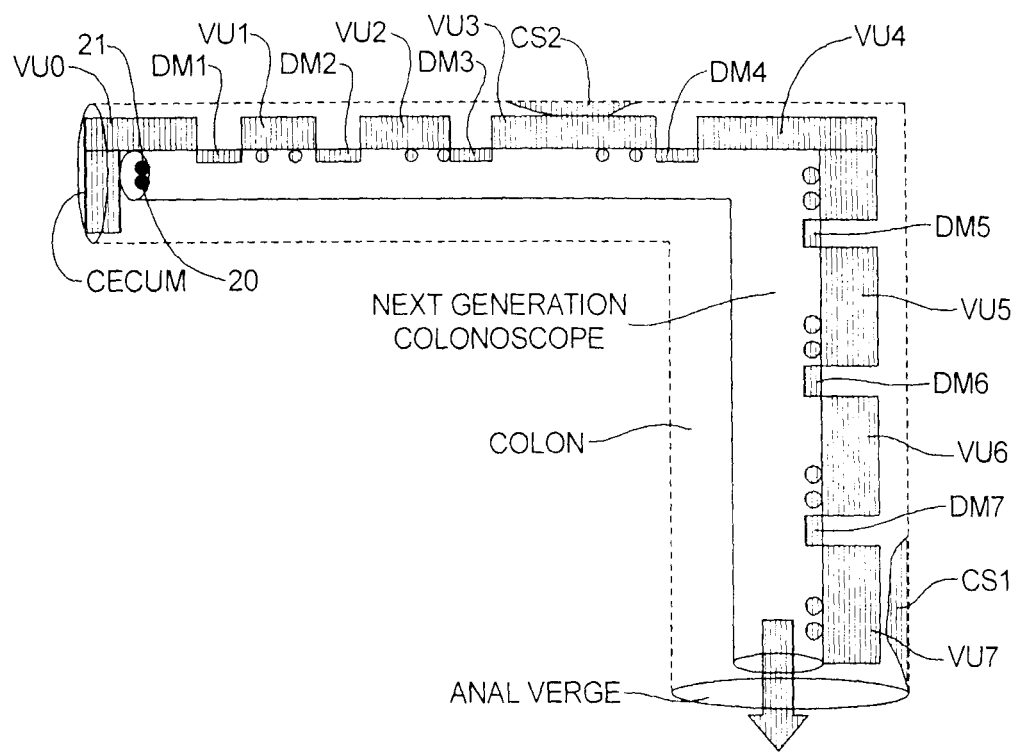
FIG. 21A is a view of the 'next generation colonoscope' inside the colon wherein it is positioned at the desired end point (cecum).
Figure 21B:
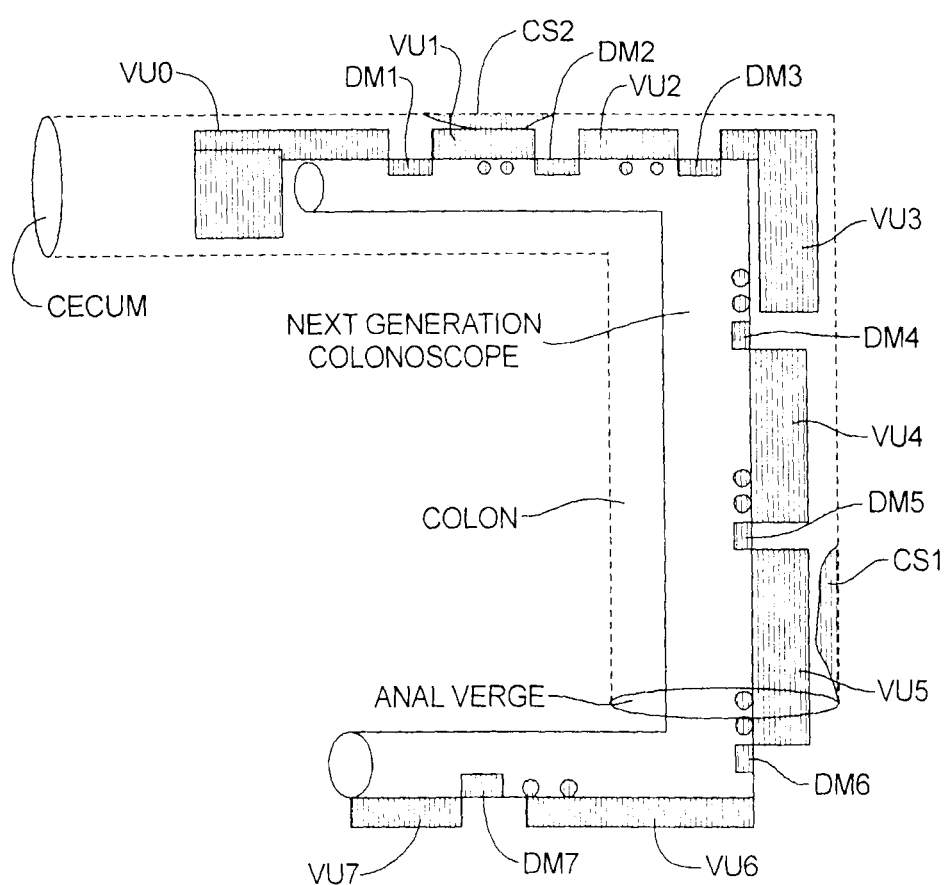
FIG. 21B is a view of the 'next generation colonoscope' inside the colon; wherein it has been partially withdrawn from the desired end point (cecum) during examination of the colon. It illustrates that the 'next generation colonoscope' enables examination various colonic segments multiple times during a single passage through the colon. It also illustrates that the 'next generation colonoscope' enables a faster examination of the colon.
Figure 22A:
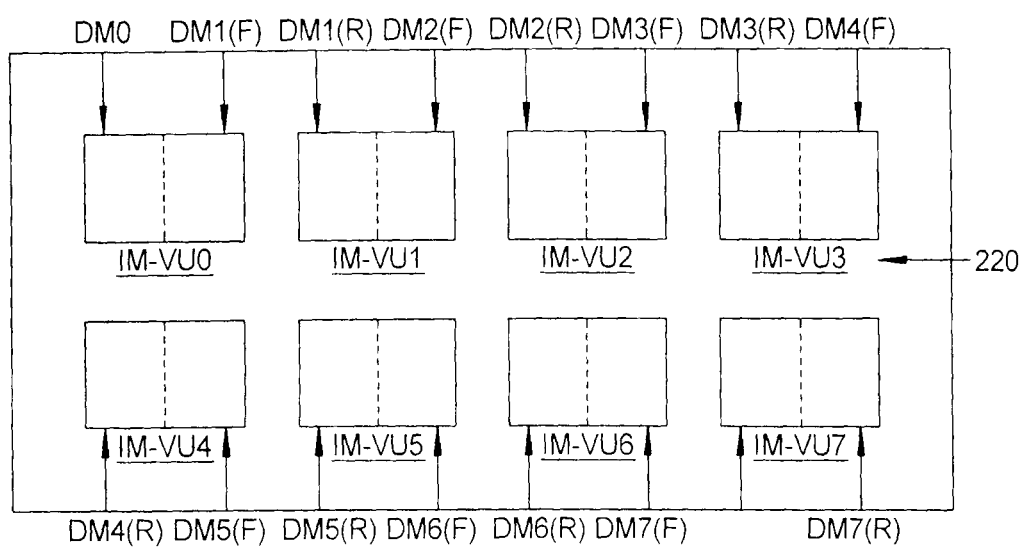
FIG. 22A is a view of the display unit displaying images from the 'next generation colonoscope' wherein each image lens of the said 'next generation colonoscope' has a separate picture.

The 'dual view modules' that have so far been discussed; are all retractable. This is done to ensure that the shaft of the 'next generation colonoscope' remains smooth in order to facilitate safe insertion into the colon. However, a non retractable 'dual view module' (DM) can also be used; as illustrated in FIG. 20. The non retractable 'dual view modules' (DM) consists of a solid hemisphere. It is attached perpendicular to the long axis of the shaft of the 'next generation colonoscope'. The proximal face (102) of the hemisphere contains the rear image lens (103) and the rear illumination bulb (104); and the distal face (101) of the hemisphere contains the forward image lens (105) and the forward illumination bulb (106). Electrical cables (107 & 108) connect the rear and forward image lens (103 & 105) to an image processor; and the rear illumination bulb (104) and the forward illumination bulb (106) to a power source. The rear image lens (103) and the rear illumination bulb (104) face backwards and give a rear view; and the forward image lens (105) and the forward illumination bulb (106) faces forwards and gives a forward view. The hemispheres appear as bumps on the shaft of the 'next generation colonoscope'. Instead of a smooth surface, the shaft now has a bumpy surface. To enable safe and painless insertion of the 'next generation colonoscope' into the colon, it is recommended that the 'dual view modules' (DM) not protrude too much outside of the shaft Operation:

Once the colonoscope reaches the desired end point; which usually is the cecum; the 'dual view modules' may be deployed using an actuator located on the handle of the 'next generation colonoscope' as shown on FIG. 21A. Either all or selected 'dual view modules' can be deployed using the actuator. The 'dual view modules' are numbered sequentially; distal to proximal; which in the preferred embodiments is from DM1-DM7, as shown in FIGS. 3, 21A & 21B; DM1 being the distal most and DM7 being the proximal most 'dual view module'. Deployment of a 'dual view module' activates its image lens and illumination bulbs; and positions its forward and rear image lens to visualize the corresponding 'view unit'. The field of view under the rear and forward image lenses of adjacent 'dual view modules' (DM) is referred to as a 'view unit'. In the illustrated example shown in FIGS. 21A & 21B; the 'view units' are numbered; distal to proximal; from VU0-VU7; VU0 corresponding to the area under the field of view of the main image lens and the forward image lens of the 'dual view module' #1 (DM1); VU1 corresponding to the area under the field of view of the rear image lens of 'dual view module' #1 (DM1) and forward image lens of 'dual view module' #2 (DM2); and so on. Now referring to FIGS. 21A, 21B & 22; we illustrate the examination of colon using the 'next generation colonoscope'. Once the 'next generation colonoscope' reaches the desired end point, the 'dual view modules' (DM1-DM7) are deployed and images are viewed on a display unit (220); such as a computer monitor, television screen and the like. Image from each image lens is viewed separately; and images from corresponding image lenses forming a 'view unit' are paired together. For example, as shown in FIG. 22A, image #2 (IM2) is a view of the 'view unit' #2 (VU2); comprising of image from the forward image lens of the 3rd dual view module (DM3(F)) and image from the rear image lens of the 2nd dual view module (DM2(R)). To make the visualization of a colonic segment, simpler, the images from the corresponding image lenses of a 'view unit' can be combined, using an image processor and image processing software, to give a consolidated image; as shown in FIG. 22B. The image processor and the image processing software are programmed to edit the images from corresponding image lenses of a view unit such that the image characteristics such as color, brightness, contrast of the two images from the corresponding lenses of the 'view unit' such that the consolidated image is of uniform and optimal quality. The consolidation process may include creating a histogram for each of RGB colors for the image from the first image receiver and a histogram for each of the RG8 colors for the image from the second image receiver and thereafter adjusting the gamut of each histogram of the image from the first imaging device to match the gamut of the corresponding histogram of the image from the second imaging device. The process then uses gamma coefficients to adjust a color level of each histogram of the image from the first image receiver to match a color level of the corresponding histogram of the image from the second imaging receiver. When images from first and second image receivers are consolidated, other information such as patient demographics of the two images are also consolidated into the consolidated images. Such feature is required for consolidation of images to occur. Referring again to FIG. 22B, image #2 (IM-VU2) is a consolidated display of images of 'view unit' #2, which in turn comprises of images from the forward image lens of the 3rd dual view module (DM3(F)) and rear image lens of the 2nd dual view module (DM2(R)). For a more detailed discussion of an exemplary view unit, see the discussion regarding FIGS. 25-28.

Now turning our attention back to FIGS. 21A & 21B, it is evident that the presence of multiple 'dual view modules' enables the 'next generation colonoscope' to examine a given colonic segment multiple times during a single passage through the colon. The number of times a given colonic segment will be examined will depend on the number of 'view units' (VU0-VU7) distal to the said colonic segment when the distal end of the 'next generation colonoscope' is at the desired end point. For example, as shown in FIGS. 21A & 21B, the colonic segment one (CSI) will be examined 8 times; sequentially by 'view units' VU7, VU6, VU5, VU4, VU3, VU2, VU1 and VU0; by the time the 'next generation colonoscope' is completely withdrawn from the colon. This is a huge advantage compared to the conventional colonoscopes; wherein a colonic segment is examined only once; using the main image lens (20) with its field of view (VUM). Drawing from the, conclusion of prior studies that demonstrate a higher detection rates for polyps and other lesions by repeated examination of a colonic segment (Rex D K et al; Gastroenterology. 1997; 112(1): 24-28); we conclude that the 'next generation colonoscope' will enable endoscopists to detect polyps, cancer and other lesions; that are otherwise missed by conventional colonoscopes. From FIGS. 21A & 21B it is also evident that proximal segments of the colon will be examined more times compared to the distal segments. For example, colonic segment #1 (CSI) will be examined 8 times; sequentially by 'view units' VU7, VU6, VU5, VU4, VU3, VU2, VU1 and VU0; whereas colonic segment #2 (CS2) will examined only 4 times; by view units VU3, VU2, VU3 and VU0 respectively. To maximize the examination of the distal colonic segments, we propose two solutions; 1) providing more 'dual view modules' in the distal part of the colonoscope; and 2) placing the distal 'dual view modules' closer than the proximal 'dual view modules'. In the illustrated embodiment of the 'next generation colonoscope' shown in FIGS. 3, 21A & 21B; five of the seven 'dual view modules' (DM1-DM5) have been placed in the distal half of the colonoscope; and the distal four 'dual view modules' (DM1-DM4) are placed closer together compared to their more proximal counterparts. Together, this enables the distal segments of the colon to be examined more number of times than would have been possible if the 'dual view modules' (DM1-DM7) were equally spaced apart.

We do understand that a given 'dual view module' (DM1-DM7) may not provide a complete 360 degree view of the colonic lumen to enable a complete examination of the corresponding colon segment. We propose three solutions to this problem; 1) as the 'next generation colonoscope' is pulled out of the colon, it usually a torques along its long axis; just like a conventional colonoscope. To enable complete 360 degree visualization of the colon, we recommend that this torque should be further augmented by applying additional intentional torque to the 'next generation colonoscope' during pullout. The above maneuver essentially enables each 'dual view module' (DM1-DM7) to view a given colonic segment from a different angle. We believe that by the time a given colonic segment is examined by multiple 'dual view modules' (DM1-DM7) from different angles, a complete 360 degree visualization of the said colonic segment will be obtained; 2) another way to address this problem is to provide more than one 'dual view module' (DM) at each location on the shaft of the 'next generation colonoscope'; for example two 'dual view modules' (DM), each with a 180 degree field of view; 3) yet another way to obtain a complete 360° visualization of a colonic segment is by placing each 'dual view module' (DM1-DM7) along a different longitudinal axis along the shaft of the 'dual view module' is that during pullout, different 'dual view modules' (DM1-DM7) view a given colonic segment from different angles; thereby enabling a complete 360 degree visualization of the said colonic segment by the time the 'next generation colonoscope' is completely pulled out.

Figure 21C:
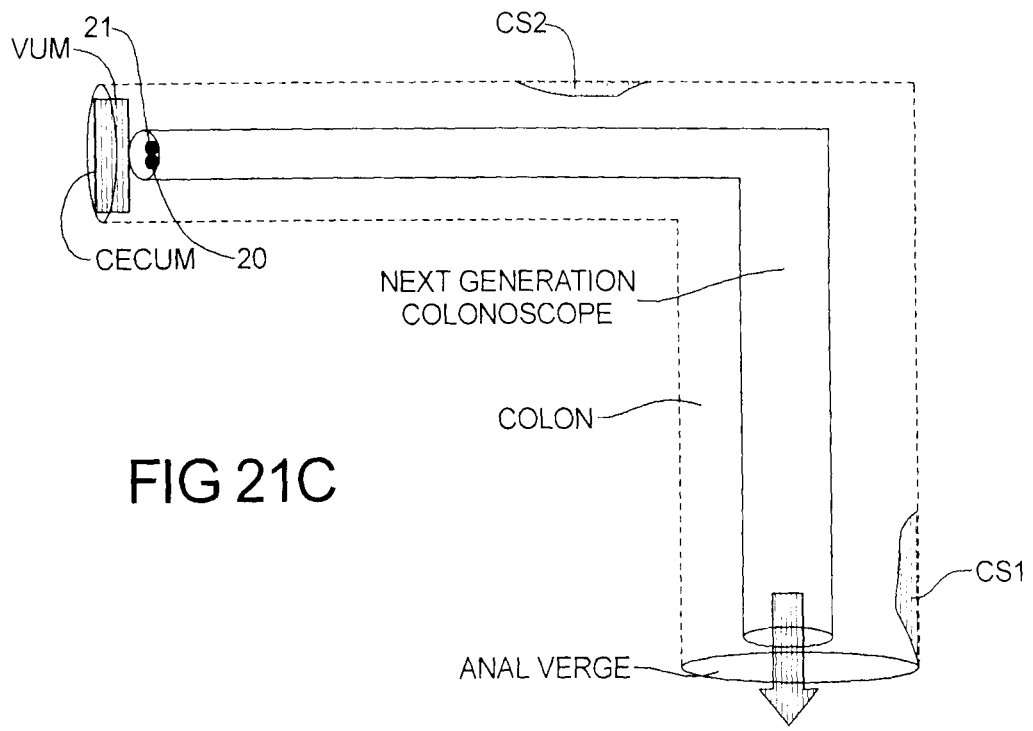
FIG. 21C shows the examination of a colon using a conventional colonoscope. It illustrates that a conventional colonoscope enables examination various colonic segments only once during a single, passage through the colon. It also illustrates that colon examination using a conventional colonoscope is a relatively slower process, compared to the 'next generation colonoscope'.

Another advantage of the 'next generation colonoscope' is that it enables faster examination of the colon; thus enabling more colonoscopies to be performed in a given period of time. This is particularly important at the present time, when there is not enough manpower to meet the colonoscopy need of many communities in the United States. Many patients who are in need for colonoscopy for colon cancer prevention; are unable get one because of the lack of enough endoscopists. One way to improve the access to colonoscopy is to design a colonoscope that will enable physicians to perform colonoscopies in a more time efficient manner. With the conventional colonoscopes, examination of the colon is done using a single image lens; the main image lens (20) as shown in FIG. 21C. During a typical colonoscopy, the endoscopist examines the colon mostly during pullout; and to some extent during insertion. After reaching the desired end point, which usually is the cecum, the colonoscope is slowly pulled out and the area under the field of view of the main image lens (20); hereby referred to as 'main view unit' (VUM); is carefully examined. The 'main view unit' (VUM) of the main image lens (20) covers a relatively small area; hence only a very small area of the colon is visualized at any given time. The endoscopist has to sequentially examine each segment of the colon under the field of view of the main image lens (VUM). As a result, examination of the entire colon is a time consuming process. The 'next generation colonoscope' enables faster examination of the colon. Once the 'next generation colonoscope' reaches the desired end point, which usually is the cecum, the 'dual view modules' (DM1-DM7) are deployed. At this point; as shown in FIGS. 21A & 21B; the total area of the colon under the field of view of a fully deployed 'next generation colonoscope' is the sum of all 'view units' (VU0+VU1+VU2+VU3+VU4+VU5+VU6+VU7); which is far greater than the area under the field of view of a conventional colonoscope at any given time; which is only the 'main view unit' (VUM). The end result of examination by a 'next generation colonoscope' is that by the time the most proximal 'dual view module' (DM7) is outside of the anal verge, the entire colon has been examined by one or more 'dual view modules' (DM1-DM7). At this point the colonoscope can be safely pulled out completely; without compromising on the completeness of the examination. It is to be appreciated that not only entire colon has been visualized by the time most proximal 'dual view module' (DM7) is outside of the anal verge, but major part of the colon has been examined more than once. It is only fair to conclude that the 'next generation colonoscope' not only enables faster examination, but also enables a more complete and thorough examination of the colon. The examination of the colon can be made even faster and more accurate by inserting the colonoscope with the 'dual view modules' (DM1-DM7) fully deployed. This will enable visualization of a given segment of the colon both during insertion and pullout. The end result of this practice will be that a given segment of the colon will be examined more times; compared to when the 'dual view modules' (DM1-DM7) are deployed only during pullout.

As shown in FIGS. 3, 21A & 21B; each, 'view unit' (VU1-VU7) of the next generation colonoscope' is serviced by an air/water channel (AWC1-AWC7)) and an instrument channel (IC1-IC7). The air/water channels (AWC1-AWC-7) and the instrument channels (IC1-IC7)are numbered, distal to proximal, which in the preferred embodiment is from 1-7. To simplify the operation of the 'next generation colonoscope', the numbering of the air/water channels (AWC1-AWC7) and the instrument channels (IC1-1C7) is similar to that of the 'view units' (VU1-VU7). For example, in the illustrated embodiment, air/water channel (AWC) #2 (AWC2) will need to be engaged to insufflate air in area under the field of view of the 'view unit' #2 (VU2). Similarly, instrument channel #2 (IC2) will need to be engaged to perform surgical procedures or apply suction in area under the field of view of the 'view unit' #2 (VU2). Because of the similar numbering pattern of the 'view units' (VU1-VU7), air/water channels (AWC1-AWC7) and instrument channels (IC1-1C7), operation of the 'next generation colonoscope' is fairly simple and straightforward. It is also evident from FIGS. 3, 21A & 21B; the view unit #0 (VU0) is serviced by the main instrument channel (24) and the main air/water channel (25).

A major advantage of the 'next generation colonoscope' is that it enables surgical procedures to be performed at the same time lesions are detected. It is critically important to remove a lesion, such as a polyp, at the same time it is detected during colonoscopy, as subsequent examination may fail to detect the said polyp, especially if it is small. With the 'next generation colonoscope' this is made possible by the presence of a separate instrument channel (24, IC1-IC7) for each 'view unit' (VU0-VU7). Once a polyp is detected in an area under the field of view of a given 'view unit' (VU0-VU7), the corresponding instrument channel (24, IC1-IC7) is engaged using an actuator (not shown) located on the handle (4). An appropriate surgical instrument is passed through the main instrument channel (24); which is then automatically guided into the said engaged instrument channel (IC1-IC7). To operate in an area under the field of view of 'view unit' #0 (VU0), the main instrument channel (24) and the main instrument channel outlet (21) is used. The surgical instrument is then used to perform surgical procedures in the area under the field of view of the said 'view unit' (VU0-VU7) where the said lesion was detected.

Figure 23C:
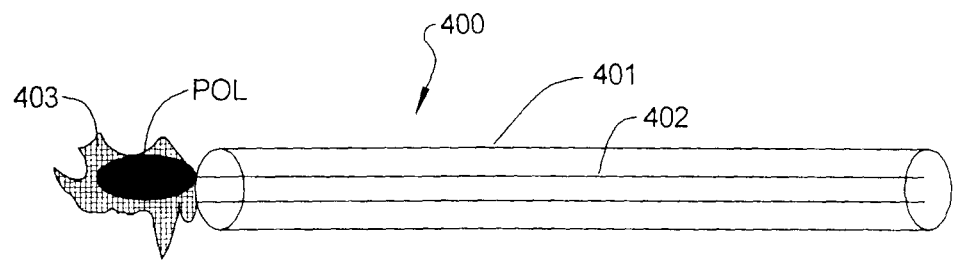
FIG. 23C shows removal of a large colonic polyp using a conventional 'polyp retrieval assembly' wherein the said polyp is firmly grasped within the net; the introducer is pulled into the sheath; following which the colonoscope with the 'polyp retrieval assembly' inside it is pulled out.

Another advantage of the 'next generation colonoscope' is that multiple polyps can be removed in a single passage through the colon. Presently, when a polyp is identified, it is cut off from the colon using one of many techniques, using a biopsy forceps or a snare. If a polyp is smaller than the diameter of the main instrument channel (24), it is retrieved by pulling it through the said main instrument channel (24). If the polyp size is greater than the diameter of the main instrument channel (24), a 'polyp retrieval assembly' (400); shown in FIG. 23A; is used. FIG. 23A shows a conventional 'polyp retrieval assembly' (400); whereas FIGS. 23B & 23C show the present method of polyp (POL) retrieval using a conventional colonoscope. The 'polyp retrieval assembly' (400) comprises of an introducer (402) and a net (403) encased in a sheath (401). When a polyp (POL) has to be removed from inside the colon, the 'polyp retrieval assembly' (400) is passed through the main instrument channel (24) to the location of the said polyp (POL). The introducer (402) is then advanced which pushes the net (403) out of the sheath (401) and deploys it. The deployed net (403) is then maneuvered to engage the said polyp (POL). Once the polyp (POL) is engaged, the introducer (402) is pulled back into the sheath (401) as far as possible. The result of this maneuver is that the said polyp (POL) is securely grasped within the net (403). The colonoscope is then pulled out with the 'polyp retrieval assembly' (400) still inside the main instrument channel (24). When the colonoscope is completely out of the colon, the introducer (402) is re advanced to loosen the net (403) and the polyp (POL) is manually captured and sent to a pathologist. The 'polyp retrieval assembly' (400) is then completely pulled out of the main instrument channel (24). With the current 'polyp retrieval assembly' (400) only one polyp can be pulled out at one time If more than one polyp is found during colonoscopy, the colonoscope has to be reinserted into the colon and advanced to the location of the said polyp. As evident from the above discussion, the more the number of polyps found, the more complicated the process gets. The shortcomings of the present system are; 1) it requires multiple insertions; which significantly increases the risk of complications like perforation and bleeding; 2) it is labor intensive and time consuming; and 3) even more concerning is the fact that a polyp that is detected on initial examination; may not be found during subsequent examinations.

We propose three methods which can be used with the 'next generation colonoscope' to address the shortcomings of the present method. 1) The 'next generation colonoscope' has multiple instrument channels (IC1-IC7). Even while one instrument channel (IC1-IC7) is engaged with a 'polyp retrieval assembly' (400); other instrument channels (IC1-IC7) remain free to remove other polyps. In order to use more than one instrument channel (IC1-IC7) and/or to pass more than one surgical instrument, the diameter of the main instrument channel (24) and/or that of the surgical instruments may have to be altered (24); 2) the second method includes suctioning the polyp into the empty 'dual view module bay' (the empty space in the shaft of the 'next generation colonoscope when the corresponding 'dual view module' (DM1-DM7) has been deployed); using suction through the instrument channel (IC1-IC7). Alternatively, a separate suction outlet can be provided in each 'dual view module bay' for this purpose. Once the polyp is securely suctioned in the 'dual view module bay', the colonoscope is pulled out. The polyp is retrieved when the said 'dual view module bay' is outside of the anal verge; 3) the third method involves changing the make, configuration and design of the 'polyp retrieval assembly' (400), which is discussed next.

Figure 24A:
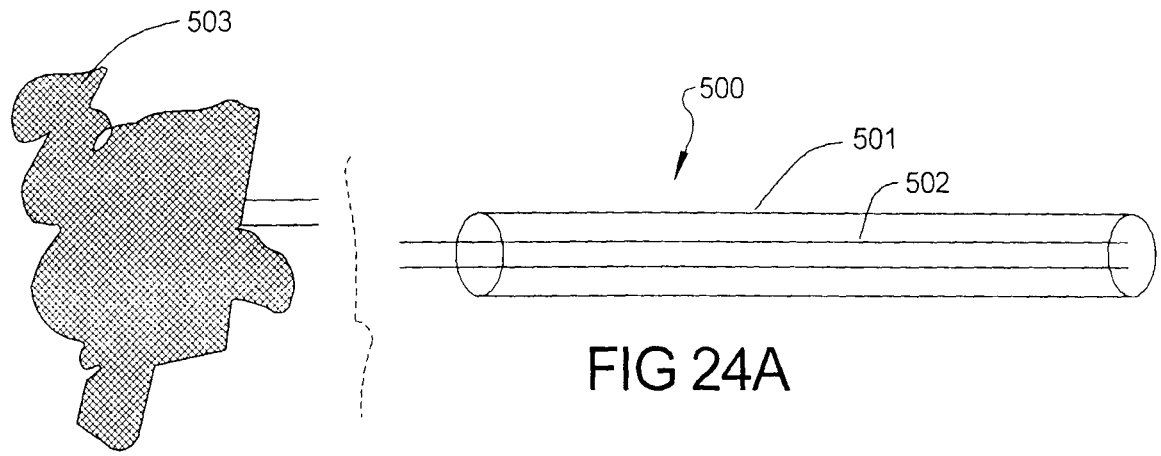
FIG. 24A is a view of the 'next generation polyp retrieval assembly' and highlights that the net is detachable from the introducer.
Figure 24B:
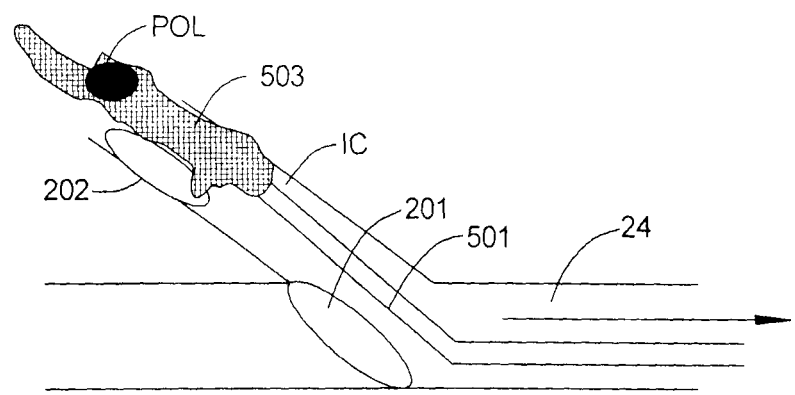
FIG. 24B shows removal of a large colonic polyp using a 'next generation polyp retrieval assembly' wherein the said polyp is grasped within the net and the net is pulled into an instrument channel of the 'next generation colonoscope'.
Figure 24C:
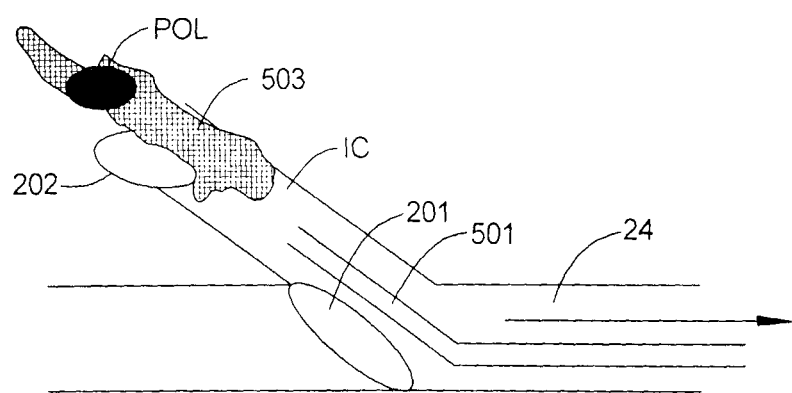
FIG. 24C shows removal of a large colonic polyp using a 'next generation polyp retrieval assembly' wherein the said polyp is grasped within the net and the net has been pulled as much as possible into an instrument channel of the 'next generation colonoscope'. The exit valve of the said instrument channel has been engaged to stabilize the net within the said instrument channel; the net has been detached from the introducer; and the introducer with the overlying sheath is being pulled out of the main instrument channel of the 'next generation colonoscope'

We propose a 'next generation polyp assembly' (500) as shown in FIG. 24A; which is optimally designed to be used with the 'next generation colonoscope'. It comprises of a net (503) attached to an introducer (502); encased in a sheath (501). In contrast to the conventional 'polyp retrieval assembly' (400), the net (503) of the 'next generation polyp retrieval assembly' (500) can be detached from the introducer (502) using an actuator located on proximal end of the introducer (502), as shown in FIG. 24A. The method of removing a polyp (POL) using the 'next generation polyp retrieval assembly' (500) is shown in FIGS. 24B & 24C. Once a polyp (POL) is grasped in the net (503), the introducer (502) is pulled back, which brings the polyp (POL) and the net (503) as close as possible to the instrument channel (IC). At this time, the proximal end of the net (503) is inside the said instrument channel (IC). The net (503) is then separated from the introducer (502) using the actuator on the proximal end of the introducer (502); subsequent to which the introducer (502) and the overlying sheath (501) is pulled out of the main instrument channel (24). This leaves the main instrument channel (24) free to be used for other surgical procedures during the same passage. Once the proximal part of the net (503) is trapped inside the instrument channel (IC), it is important to secure its position to prevent it from falling off. To achieve this goal, the exit valve of the instrument channel (202) is utilized. The control valve assembly of the instrument channel is closed once the introducer (502) is pulled out of the instrument channel (IC). The exit valve (202) grasps the net (503) that is nestled in the instrument channel (IC). This stabilizes the net (503); with a polyp (POL) inside; during pullout of the 'next generation colonoscope'. Once the said instrument channel (IC) is outside of the anal verge, the exit valve (202) is opened and the net (503), along with the captured polyp (POL) is retrieved.

Figure 25:
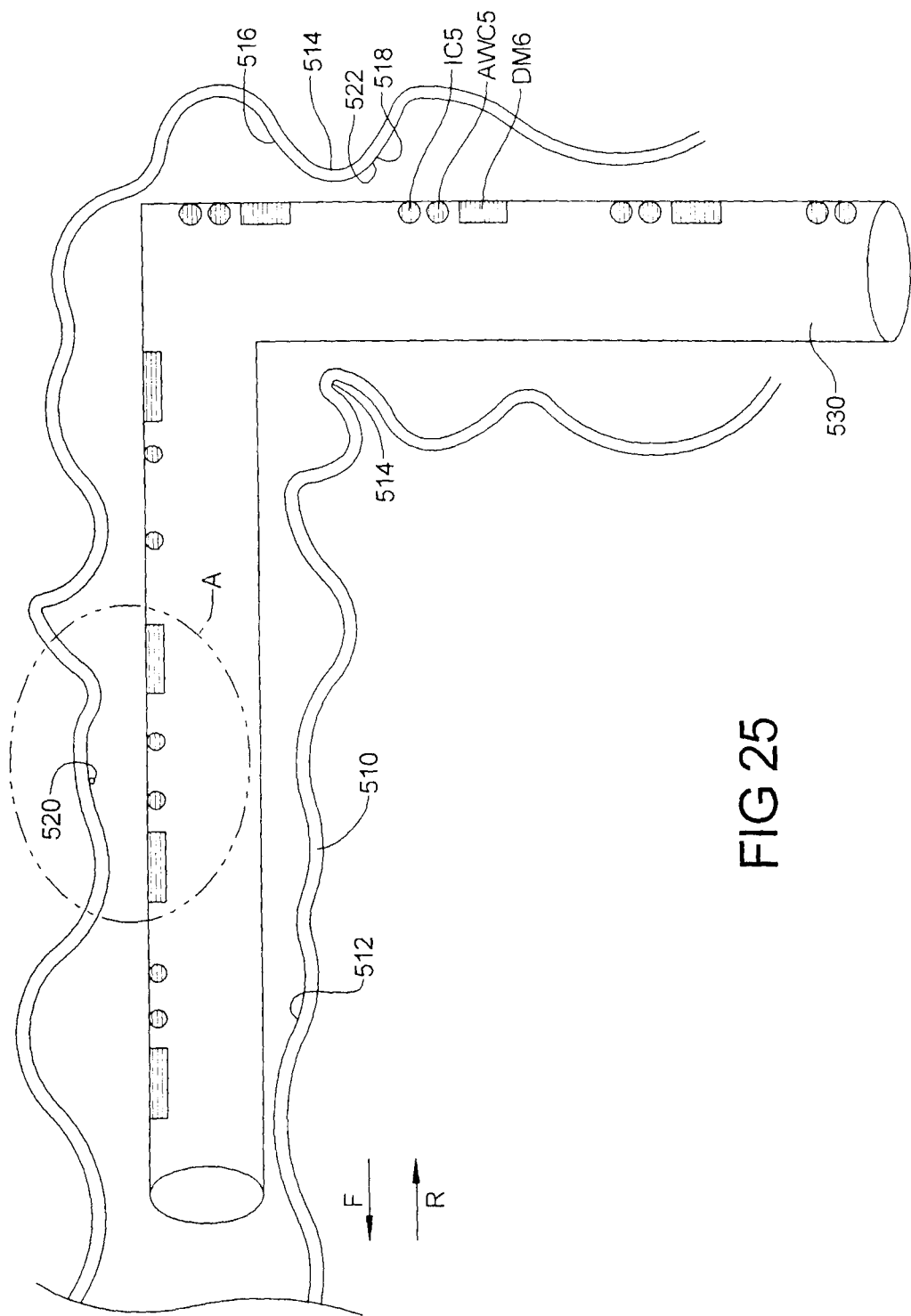
FIG. 25 is partially sectioned view of a colon (with section lines removed for clarity) and a colonoscope according to an embodiment.

FIG. 25 illustrates a colon (510) having a deformed generally tubular inner surface (512) that includes a plurality of inner folds (514) defining at least a first surface (516) and a second surface portion (518). The inner surface (512) is illustrated with a first polyp (520) extending therefrom, and a second polyp (522) extending from the second surface portion (518). A colonoscope (530) is interposed within the colon (510). The colonoscope (530) is similar to the scope of FIG. 3 and includes a first image receiver (DM3F), a first image receiver illumination source (534), a second image receiver (DM2R), a second image receiver illumination source (536), a main instrument channel (24), second instrument channel branch IC2, a second IC valve (201), a main air-water channel (25), a second air-water channel branch AWC2, and a second air-water valve (301). In the embodiment illustrated, the illumination sources (534), (536) are bulbs, although other sources of light may be used As best illustrated in FIG. 27, the first image receiver (DM3F) is positioned so as to be directed toward a first (or forward) direction F, the second image receiver (DM2R) is positioned so as to be directed toward a second (or rearward) direction R. The first direction F is generally opposite the second direction R. In the embodiment illustrated, the image receivers are lenses, although other suitable image receivers may be used.

The second IC valve (201) includes a valve disk (222). The valve disk (222) is moveable between a first position (shown in phantom) where the second instrument channel branch IC2 is blocked from the main instrument channel. 24 and a second position, where the second instrument channel branch (IC2) is not blocked from the main instrument channel (24). In the second position, the valve disk (222) will guide an instrument, such as the distal end of the polyp retrieval assembly (400) into the second instrument channel branch (IC2) as the distal end of the polyp retrieval assembly (400) is inserted through the main instrument channel (24), as seen in FIG. 27. When the valve disk (222) is in the first position, the valve disk (222) will guide an instrument, such as the distal end of the polyp retrieval assembly (400) so as to prevent the instrument from entering into the second instrument channel branch (IC2) as the distal end of the polyp retrieval assembly (400) is inserted, through the main instrument channel (24).

FIGS. 22A, 22B, 26 and 28 illustrate a portion of a monitor (550). The monitor (550) includes a viewscreen portion (552). The first image receiver (DM3F) receives a first image 560 and the second image receiver (DM2R) receives a second image 562. As illustrated, the first image 560 may be both displayed on the viewscreen portion (552) directly adjacent to the second image 562 to assist a user in identifying the related images. That is, some of the tissue of the colon (510) that is visible in the first image (560) is also visible in the second image (562). For example, the first polyp (520) is visible in both the first image (560) and the second image (562) since the first polyp (520) is within a line of sight of both the first image receiver (DM3F) and the second image receiver (DM2R). In the exemplary illustration of FIG. 27, the colonoscope (530) is interposed within the colon (510) such that the polyp (520) is a first distance L1 to first image receiver (DM3F) and the polyp (520) is a second distance L2 to the second image receiver (DM2R). These distances L1 and L2 are provided at least in part, to permit viewing the polyp (520) from multiple lenses while permitting access, to the polyp (520) through the second instrument channel branch IC2 and the second air-water channel branch AWC2.

Further, as shown in FIGS. 22A, 22B and 26A, the first image (560) and the second image (562) may be both displayed on the viewscreen portion (552) such that the relative orientation is the same. That is, the radial direction D as seen in FIG. 27 of the lumen is oriented in the first image (560) to be parallel to the radial direction D when viewed in the second image (562), as best seen in FIG. 26A.

As seen in the embodiment of FIG. 26B, the sideways orientation of the images from first and second image receivers (DM3F) and (DM2R) may be aligned such that the sideways orientation of the images from the viewer's perspective is similar on the view screen. That is, when the user views an instrument, such as the net (403) moving to the right (in the direction of arrow S1) in the first image (560), the user may also view the net (403) moving to the right in the second image (562). This feature may be preferred by a user as useful for the viewer to direct therapy at a lesion under view of both the first and the second image receivers. [In contrast, in FIG. 26A, when the user views an instrument, such as the net (403) moving to the right (in the direction of arrow S1) in the first image (560), the user may also view the net (403) moving to the left in the second image (562).] As such a lesion that appears on the right side on the view screen from first image receiver, may also appear on the right side of the view screen from the second image receiver. An exemplary illustration of orienting the images from first and second image receivers (DM3F) and (DM2R) from a single viewer's point of view is shown in FIG. 26B. As shown in FIG. 26B the first image (560) from the first image receiver (DM3F) is a view of the proximal section of the polyp (520) and the second image from the second image receiver is a view of the distal section of the polyp (520); both from the single viewer's point of view. As such in the illustrated example of FIG. 26B, the polyp (520) is displayed on the right side of the view screen in both the first and second images (560), (562). Such an adjustment can be performed at the level of the image receiver, image processor (15); or by providing image manipulating capability to the user to adjust the orientation of the first and second images displayed on the view screen (such as flipping the image 560 about a vertical axis, where the vertical axis is parallel to the direction D). As shown in FIG. 26B, it is evident that when images of a lesion, such as the polyp (520), in common field of view of both the first and second image receivers (DM3F) and (DM2R) are consolidated, the orientation of the first and second images may be consolidated such that the consolidated image contains first and second images oriented in similar directions, both vertically and horizontally (FIG. 26B) from a viewer's direction. This feature may be required for consolidation of the first and the second images.

Additionally, the relative sizes of the first image (560) and the second image (562) may be presented on the viewscreen portion (552) such that features such as the first polyp (520) are commensurate in size in both the first image (560) and the second image (562). That is, for example, the user may position the colonoscope (530) within the colon (510) such that the first distance L1 is about equal to the second distance L2. With the lenses of the first image receiver (DM3F) and the second image receiver (DM2R) having a similar design and adjustment, the first image (560) and the second image (562) will be generally proportional in size (as illustrated in FIGS. 26 and 28) to their distance from the corresponding image receiver. Alternatively, the first image (560) and/or the second image (562) may be altered and displayed with an item of interest, such as the polyp 520 being generally of the same size in each image when the first distance L1 is not equal to the second distance L2. As shown in FIG. 22B, it is evident that when images of a lesion, such as a polyp, in common field of view of both the first and second image receivers is consolidated, the consolidated image contains first and second images of commensurate size when equidistant from first and second image receivers. Similarly, when the polyp 520 is in field of view of both the first and second image receivers, at least one image characteristic (such as, for example, color, size, orientation, contrast, brightness etc.) of the first and second images are adjusted by the image processor (15) as desired.

In one example, the first and second images (560), (562) are displayed as shown in FIG. 26A. The image processor (15) may adjust a characteristic (such as the orientation of the direction SI) of the first image (560) to be about the same as in the second image (562). For example, the image processor (15) may flip the first image (560) about the vertical axis (generally parallel to the direction D) to be a reverse image as illustrated in FIG. 26B tio make the charateristic of orientation in the first image (560) more closely match the same characteristic in the second image (562). This manipulation is demonstrated by the arrows S1, which are pointing in opposite directions in the images of FIG. 26A and in generally the same directions in the images of 26B.

In another example, FIG. 22A illustrates that the characteristic of size of the image from the image receiver DM2R has been manipulated by the image processor (15) to be about the same size as the image from the image receiver DM3F.

Further, FIGS. 22A and 26A illustrate that the characteristic of orientation of the direction D of the image (such as the image 562 in FIG. 26A) from the image receiver DM2R has been manipulated by the image processor (15) to be about the same orientation as the image (such as the image 560 in FIG. 26A) from the image receiver DM3F. That is, when viewed on the screen 220, 520, the direction D of one image is generally parallel to the direction D of the other image.

In operation, a user will insert the colonoscope (530) within the colon (510) such that the first image receiver (DM3F) and the second image receiver (DM2R) transmit images of the inner surface (512) to the viewscreen (552) as at least one illumination source (534), (536) illuminates the inner surface (512). As best seen in FIG. 25, when the user detects an item of interest, such as the polyp (520), the user may move the colonoscope (530) (either axially, or rotationally, or both) to position the colonoscope (530) within the colon (510) so that a visible portion of the inner surface (512), such as the polyp (520), may be in the field of view of the first image receiver (DM3F) and the second image receiver (DM2R). Then, the user may decide whether to remove the polyp (520). If the polyp (520) is to be removed, the colonoscope (530) may be moved further within the colon (510) (such as positioning the colonoscope (530) such that the first distance L1 is about equal to the second distance L2).

To reposition the colonoscope (530) within the colon (510) so as to position the colonoscope (530) such that the first distance L1 is about equal to the second distance L2, the user may axially move the colonoscope (530) within the colon (510) until the polyp (520) in the first image (560) is about the same size as the polyp (520) in the second image (562). This positioning of the colonoscope (530) within the colon (510) may also ensure that the second instrument channel branch (IC2) is positioned relative the polyp (520) such that an instrument, such as the polyp retrieval assembly (400) may be guided toward the polyp (520), upon exiting from the second instrument channel branch (IC2).

In continuing the operation, the user will then move the valve disk (222) to the second position, and then guide an instrument, such as the distal end of the polyp retrieval assembly (400) through the second instrument channel branch (IC2) as the distal end of the polyp retrieval assembly (400) is inserted through the main instrument channel (24). When the distal end of the polyp retrieval assembly (400) exits the second instrument channel branch (IC2) [specifically, the net (403) guided by the introducer (402) exits the second instrument channel branch (IC2)], the net (403) is guided toward the polyp (520) while the user views the net (403) in both the first image (560) and the second image (562).

While the net (403) is guided toward the polyp (520), the polyp (520) and/or the net (403) may not be visible by one of the first image receiver (DM3F) and the second image receiver (DM2R) due to obstructions within the colon (510) or movement of the inner surface (512). In the event that the user loses sight of the polyp (520) and/or the net (403) in one of the images (560), (562), the user may be able to use the other of the images (560), (562). Further, during some procedures, the user may desire to view the image (560) and the image (562) alternately, such as when securing the net (403) to opposing sides of the polyp (520). The positioning of the image (560) directly adjacent the image (562) on the viewscreen (550) may permit the user to more easily view the images alternately since the images, in the embodiment illustrated, are positioned directly adjacent.

The user may then engage the net (403) with at least a portion of the polyp (520) by maneuvering the introducer (402). The user may then pull the introducer (402) and the net (403) back into the second instrument channel branch (IC2) as the tissue to be removed is severed from the remainder of the inner surface (512). The polyp retrieval assembly (400) may be removed from the endoscope (510), the tissue removed, and the polyp retrieval assembly (400) reinserted into the main instrument channel 24.

It will be appreciated that multiple tissue portions, such as polyps (520), (522), may be removed without axially moving the endoscope (530) within the colon (510). That is, the polyp (520) may be removed through the second instrument channel branch (IC2)and the polyp (522) may be removed through the fifth instrument channel branch (IC5).

Any person/persons familiar with prior art will understand that modifications or changes to the present invention can be made without compromising its spirit and principles. Some possible variation of the preferred embodiments of the present invention are; 1) the relative positions of the 'dual view module', air/water channel and the instrument channel can be interchanged; 2) moreover, the air/water and/or instrument channels can be positioned within the 'dual view modules'; 3) the shape, composition, design and configuration of the 'dual view module' can be modified or changed; 4) the method of deployment of the 'dual view module' can be modified; 5) in the preferred embodiments of the present invention, the 'dual view module' provides both forward and rear views, however modules with only forward or rear view can be provided; 6) although the preferred embodiments of the present invention discuss 'colonoscope' and 'colon examination'; the principles of the present invention can be applied to any endoscopic device; and endoscopic examination of any body organ or any hollow cavity; 7) in the preferred method of colon examination, the 'dual view modules' remain deployed during the entire pullout of the colonoscope. However the 'dual view modules' can be deployed and retracted any number of times during pullout. Similarly, the 'dual view modules' can be deployed and retracted any number of times during insertion into the colon; 8) the 'dual view modules' in addition to having means for deployment, can also have means to move around once it has been deployed. Means can be provided to move the 'dual view modules' up, down, left and right. This will give the endoscopist more control over determining the field of view of each 'dual view module'. The above examples are only illustrative and by no means all inclusive.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A colonoscope used to perform colonoscopy comprising:
    a single shaft interposable within a colon lumen of a human body, the single shaft extending along a longitudinal axis thereof from a distal end thereof to a proximal end thereof. the distal end of the single shaft and the proximal end of the single shaft defining a hollow channel of the single shaft extended therethrough, the hollow channel connected to and opening to one or more outlets on the distal end of the single shaft, the distal end of the single shaft being received in the colon lumen as the single shaft is being interposed within the lumen;
    a first image receiver disposed at a first location on or adjacent to the distal end of the single shaft, the first image receiver configured to receive a first image of a first observation area of the colon lumen as a part of a first original image received by the first image receiver, the first image receiver having a first field-of-view (FOV) as a result of the first image receiver being disposed at the first location in receiving the first image of the first observation area;
    a second image receiver disposed at a second location on the single shaft adjacent to the first image receiver and configured to receive a second image of the first observation area and a first image of a second observation area of the lumen as a part of a second original image received by the second image receiver, the second image receiver having a second FOV differing from the first FOV of the first image receiver as a result of the second image receiver being disposed at the second location in receiving the second image of the observation area;
    a third image receiver disposed at a third location on the single shaft adjacent to the second image receiver and configured to receive a second image of the second observation area and a first image of a third observation area of the lumen as a part of a third original image received by the third image receiver, the third image receiver having a third FOV differing from the second FOV of the second image receiver as a result of the third image receiver being disposed at the third location in receiving the second image of the first observation area;
    a fourth image receiver disposed at a fourth location on the single shaft adjacent to the third image receiver and configured to receive a second image of the third observation area of the lumen as a part of a fourth original image received by the fourth image receiver, the fourth image receiver having a fourth FOV differing from the third FOV of the third image receiver as a result of the fourth image receiver being disposed at the fourth location in receiving the fourth image of the observation area;
    a processor configured to receive both the first and second images of each of the first, second, and third observation areas and form a one of a corresponding first, second, and third displayable consolidated image, each of said corresponding consolidated images including both the first and second images of said observation area, the first and second images of said observation area positioned adjacent to each other within said consolidated image, said consolidated image indicating a lesion in the observation area as being not visible in one of the first and second images of the observation area but being visible in the other of the first and second images of the observation area due to obstructions within the lumen as well as the FOVs of adjacent image receivers differing from each other;

a first instrument channel outlet positioned between the first image receiver and the second image receiver;

a second instrument channel outlet positioned between the second image receiver and the third image receiver;

a third instrument channel outlet positioned between the third image receiver and the fourth image receiver; and an outlet selection actuator, wherein each of said outlets configured to be connected to and selectively open to the hollow channel in response to a selecting operation of the outlet selection actuator and to channel, via the hollow channel, a lesion-removal instrument to remove the lesion indicated in the consolidated image, each of said instrument channel outlets disposed in such a location on or adjacent to the single shaft that the lesion-removal instrument, in being passed through the instrument channel outlet to reach the lesion, is within at least one of the first and second FOVs of the image receivers adjacent said instrument channel outlet.

2. The colonoscope of claim 1, wherein a dimension of the first image of the observation area is generally the same size as a dimension of the second image of the observation area.

3. The colonoscope of claim 1, wherein the processor is further configured to manipulate a characteristic in the first image of the observation area to be more closely matching a characteristic in the second image of the observation area.

4. The colonoscope of claim 3, wherein the characteristic in the first image of the observation area comprises at least one of color, size, orientation, contrast, and brightness.

5. The colonoscope of claim 1, wherein the first FOV covers a first area lying in front of the distal end of the single shaft such that a line segment connecting a first point in the first area and a second point on the distal end of the single shaft forms a zero angle with the longitudinal axis in a forward direction pointing from the proximal end of the single shaft to the distal end of the single shaft.

* * * * *